(12) United States Patent
Kasid et al.

(10) Patent No.: US 7,074,807 B2
(45) Date of Patent: Jul. 11, 2006

(54) COMPOSITIONS AND METHODS FOR INDUCING CELL DEATH

(75) Inventors: Usha Kasid, Rockville, MD (US); Simeng Suy, Richmond, VA (US)

(73) Assignee: Georgetown University, Washington, DC (US)

( * ) Notice: Subject to any disclaimer, the term of this patent is extended or adjusted under 35 U.S.C. 154(b) by 80 days.

(21) Appl. No.: 10/382,317

(22) Filed: Mar. 13, 2003

(65) Prior Publication Data

US 2004/0024025 A1  Feb. 5, 2004

Related U.S. Application Data

(63) Continuation of application No. 09/720,361, filed as application No. PCT/US99/14173 on Jun. 21, 1999, now abandoned.

(60) Provisional application No. 60/090,878, filed on Jun. 26, 1998.

(51) Int. Cl.
*A61K 31/445* (2006.01)
(52) U.S. Cl. .................................................. 514/315
(58) Field of Classification Search ................. 514/315
See application file for complete search history.

(56) References Cited

U.S. PATENT DOCUMENTS

| | | | |
|---|---|---|---|
| 5,622,994 A | 4/1997 | Carney et al. | |
| 5,741,893 A | 4/1998 | Hsia | |
| 5,906,996 A | 5/1999 | Murphy | |

FOREIGN PATENT DOCUMENTS

WO   WO 98/53835   12/1998

OTHER PUBLICATIONS

HCAPLUS DN 103:198, Luzhkov, Theochem, 22, 165-172 (1985), abstract only.*
Goodman & Gilman's, The Pharmacological Basis of Therapeutics, Ninth Edition, McGraw-Hill, (1996), Calabresi et al., Chemotherapy of Neoplastic Diseases, pp. 1225-1230.*
Metodiewa et al., Anticancer Research, 18(1A), 1998, p. 369-377.
Gariboldi et al., Free Radical Biology and Medicine, 24(6), 1998, p. 913-923.
Chemabs, AN 110:94959, Protsenko et al., Khim.-Farm. Zh., 22(7), 1988, p. 803-805 (abstract only).
Chemabs, AN 116:128594, Zhang et al, Gaodeng Xuexiao Huaxue Xuebao, 12(8), 1991, p. 1056-1060 (abstract only).
Monti et al., Pharmacology and Experimental Therapeutics 39:90, 1998.
Monti et al. Procs. of the American Assoc. for Cancer Reseacrh, 38:193, 1997.
Monti et al. Procs. of the American Assoc. for Cancer Reseacrh, 36:387, 1995.
Shimabukuro et al., Proc. Natl. Acad. Sci. USA, vol. 95, 1998, p. 2498-2502.
Arnockzy et al., 47th Annual Meeting, Orthopaedic Research Society, 2001, San Francisko, California.

* cited by examiner

*Primary Examiner*—Christopher S. F. Low
*Assistant Examiner*—C. Delacroix-Muirheid
(74) *Attorney, Agent, or Firm*—Pillsbury Winthrop Shaw Pittman LLP

(57) ABSTRACT

The present invention relates to methods for inducing cell death via activation of the caspase, SAPK, and apoptotic signaling cascades in a cell comprising administering to a cell a composition comprising tempo in a amount sufficient to induce death of said cell.

5 Claims, 16 Drawing Sheets

4- Hydroxy-TEMPO

TEMPO

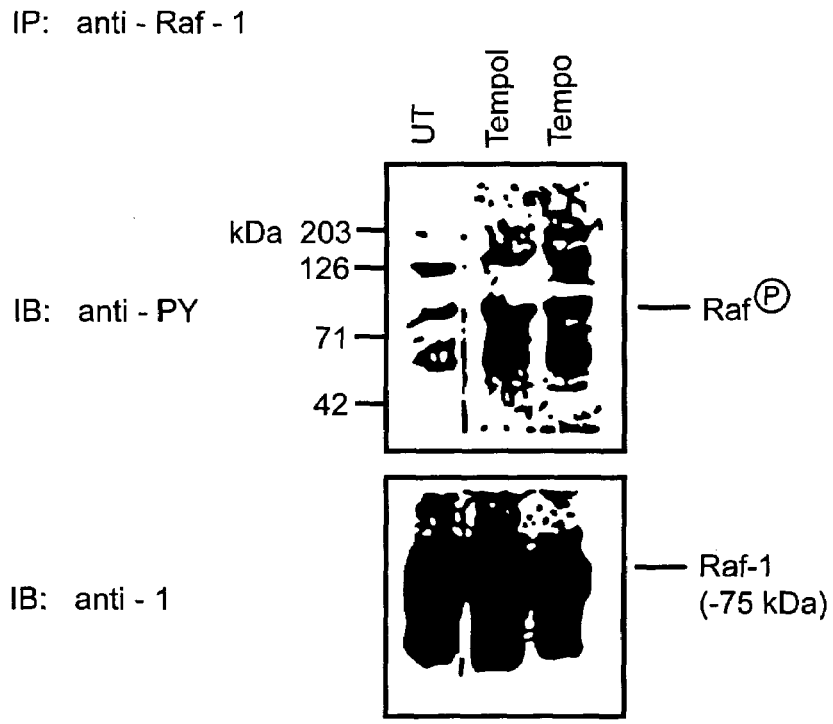
FIG. 3A
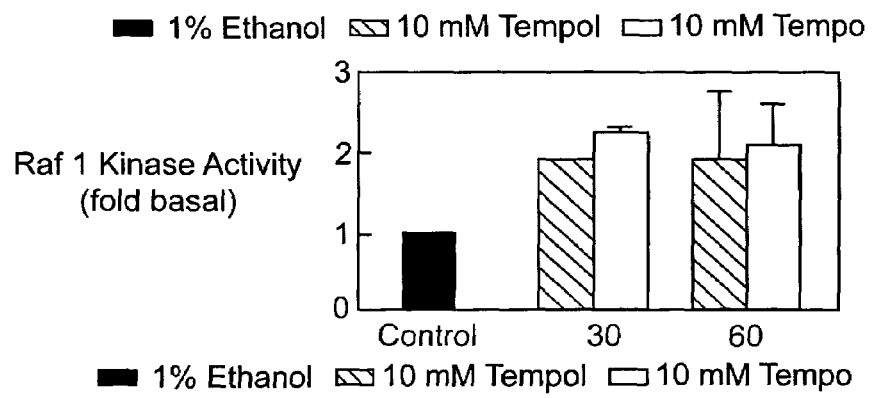
FIG. 3B1
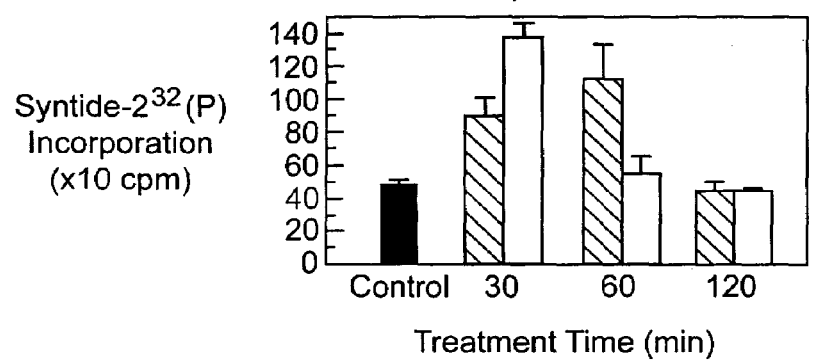
FIG. 3B2

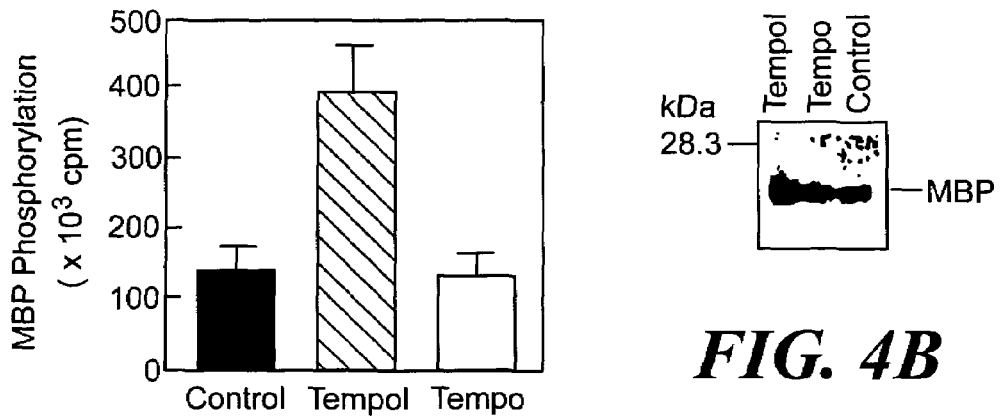
FIG. 4A
FIG. 4B
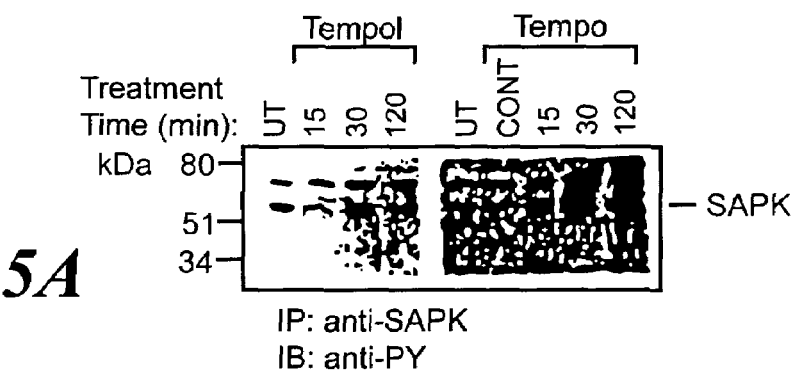
FIG. 5A
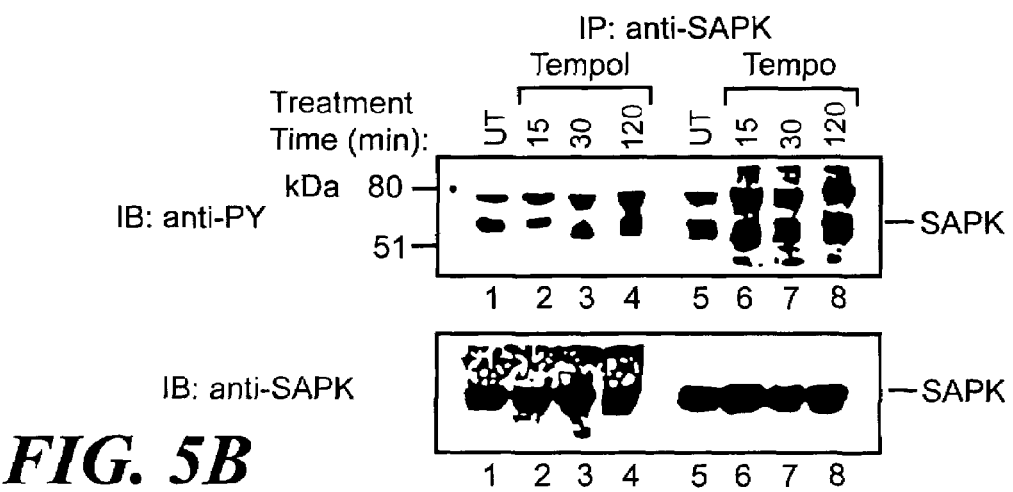
FIG. 5B

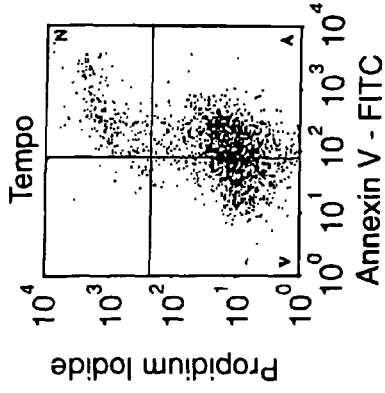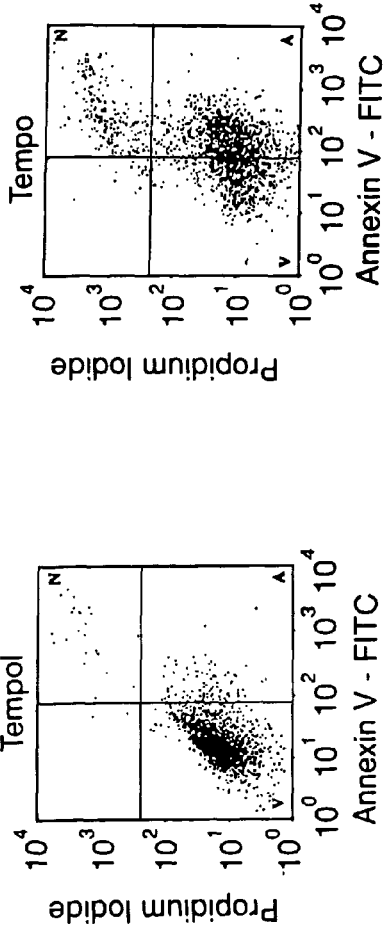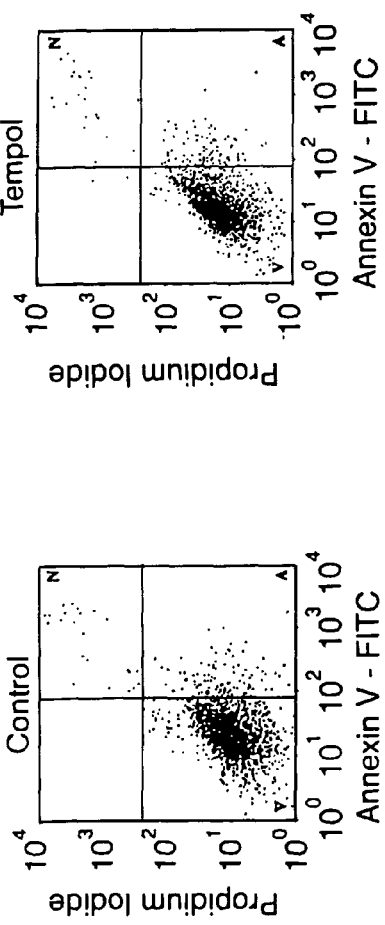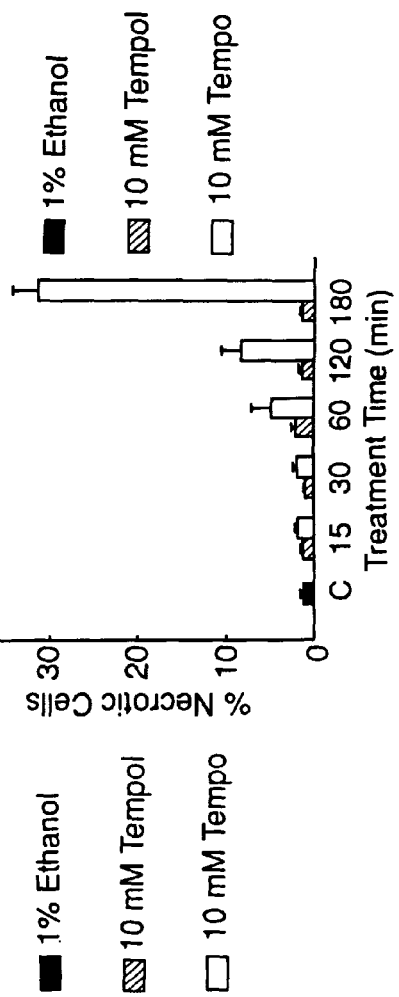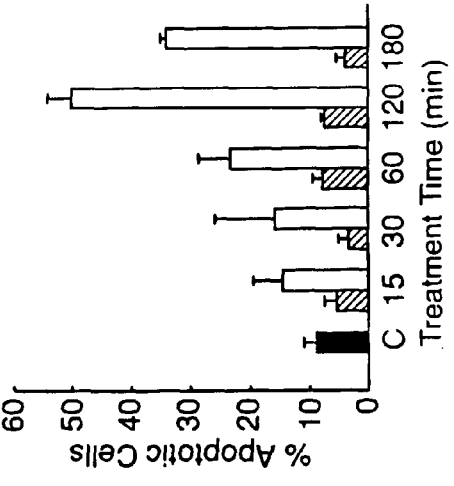

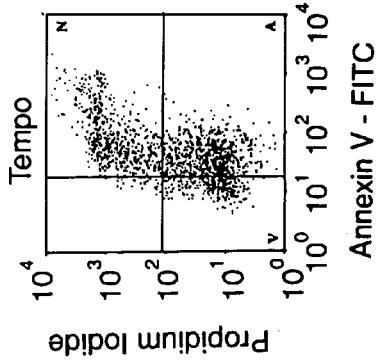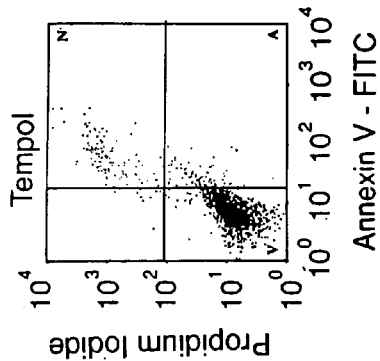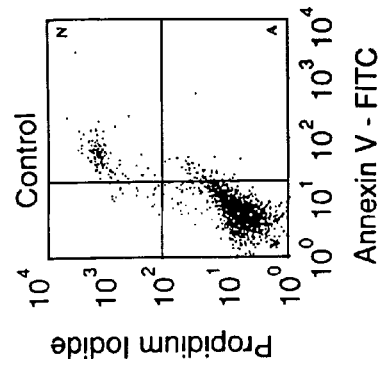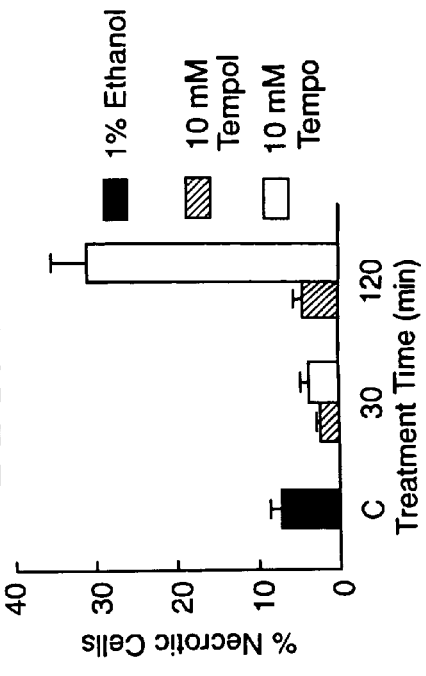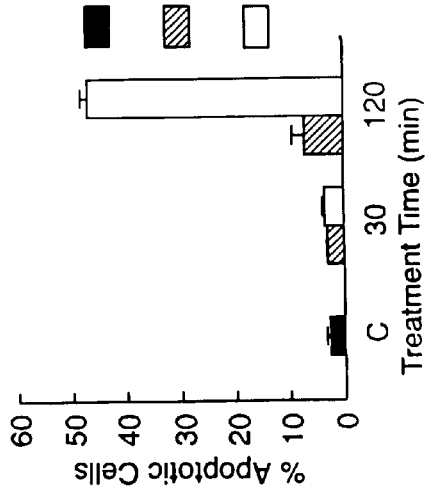

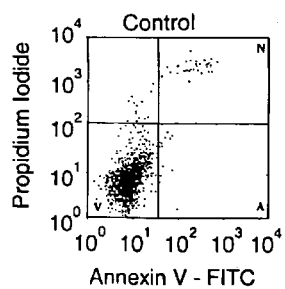
FIG. 7E1
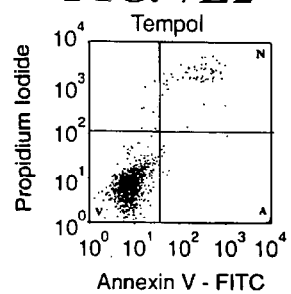
FIG. 7E2
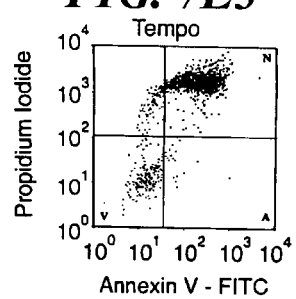
FIG. 7E3
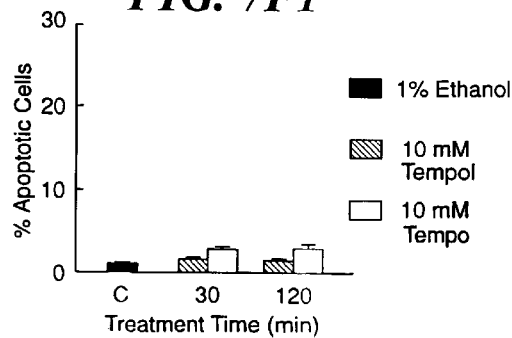
FIG. 7F1
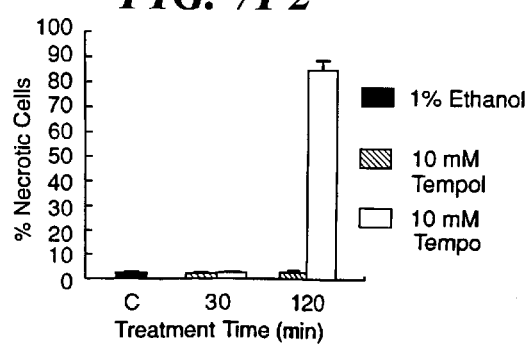
FIG. 7F2

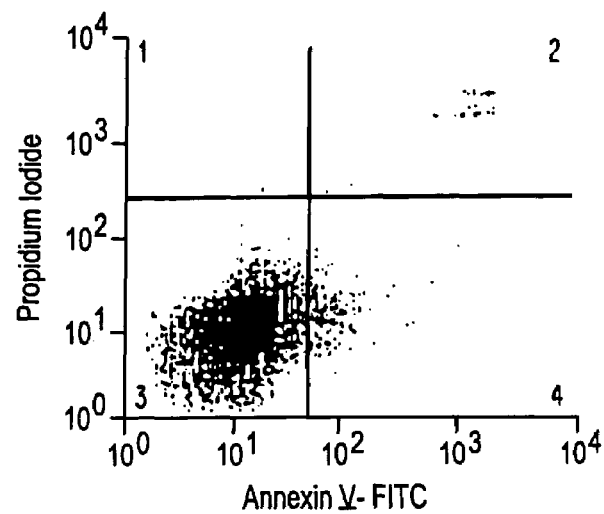
FIG. 9A1
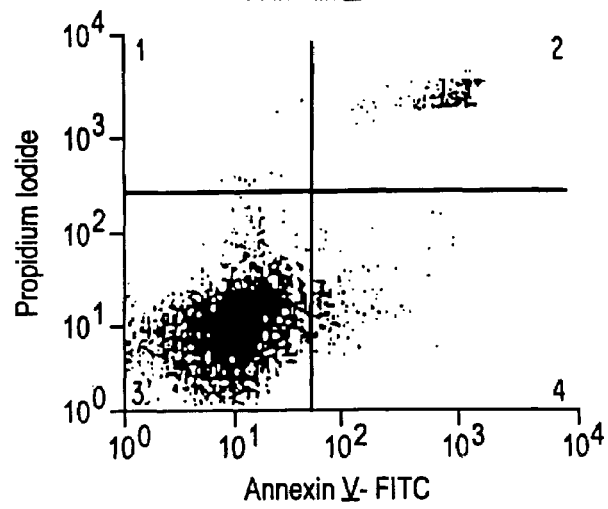
FIG. 9A2
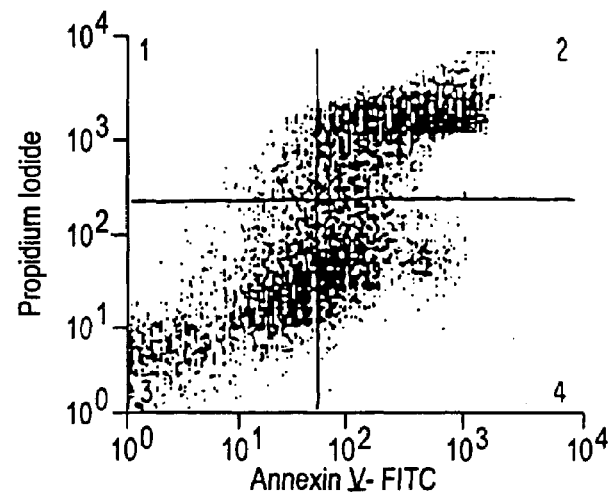
FIG. 9A3

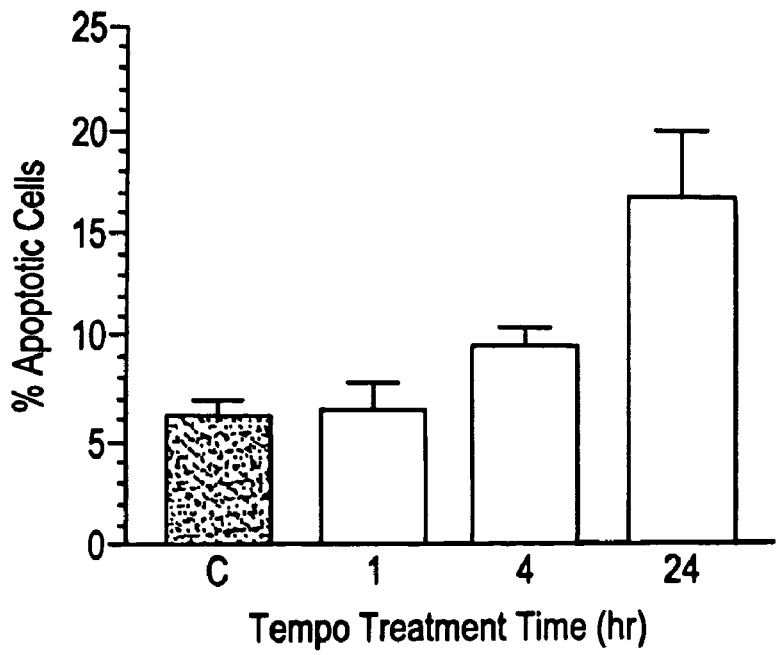
FIG. 9B1
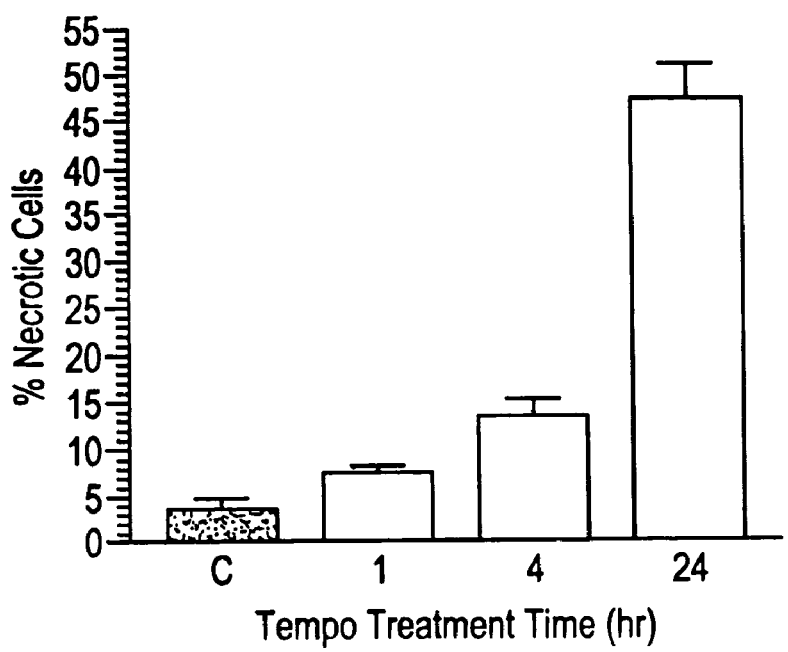
FIG. 9B2

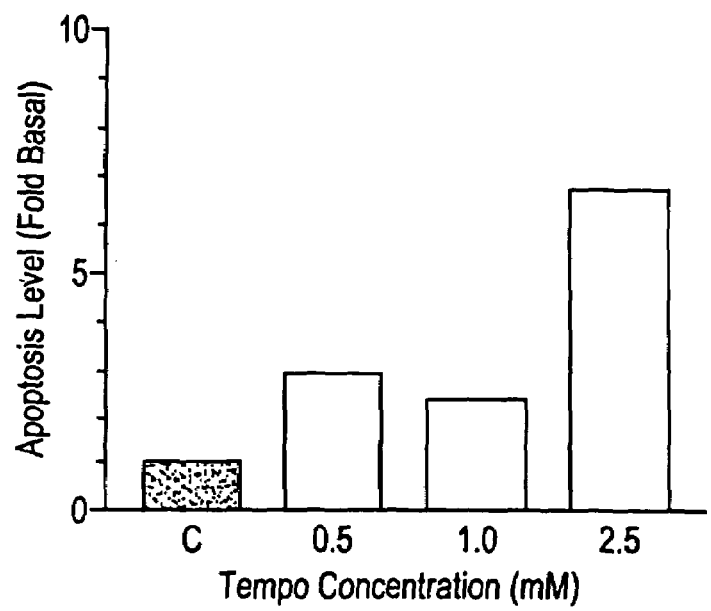
FIG. 9C1
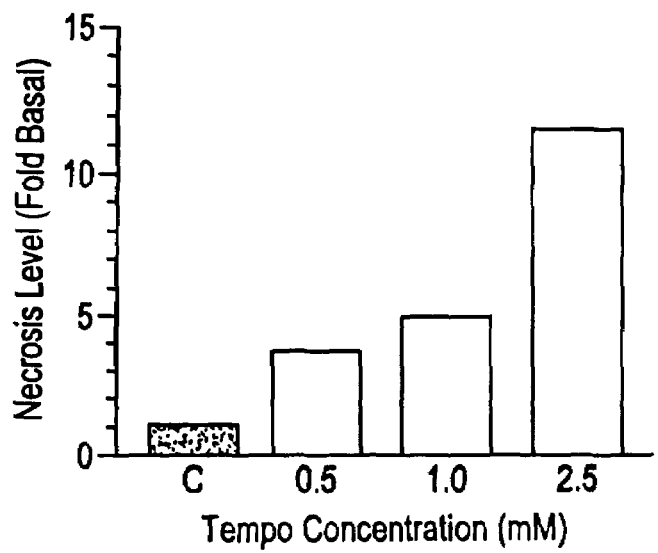
FIG. 9C2

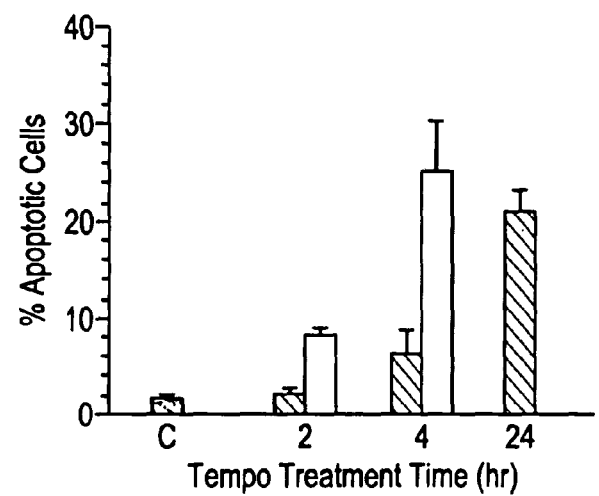
FIG. 9D1
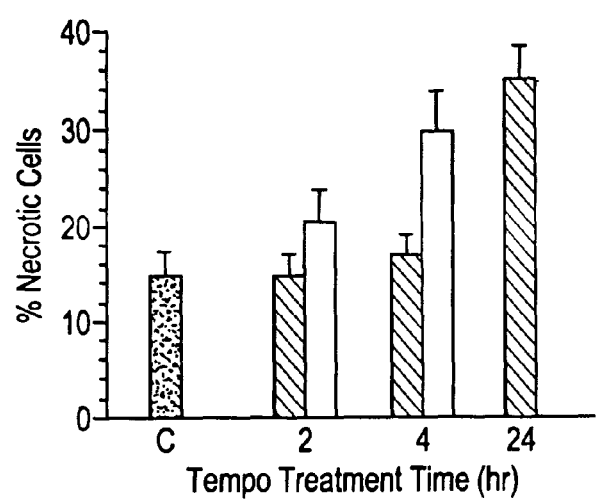
FIG. 9D2

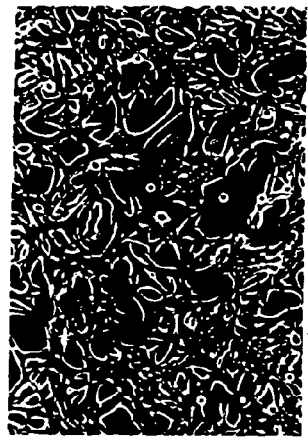
FIG. 11A2
Tempo
Treatment Time (hr) 8
FIG. 11B2
Tempo
Treatment Time (hr) 24
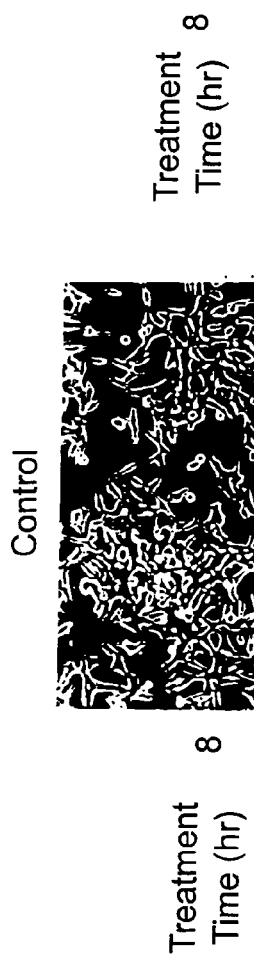
FIG. 11A1
Control
Treatment Time (hr) 8
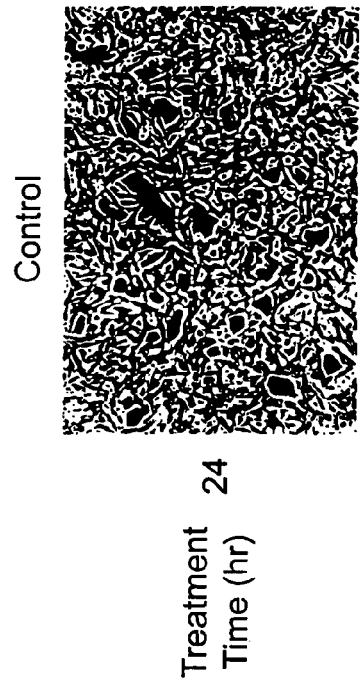
FIG. 11B1
Control
Treatment Time (hr) 24

FIG. 12A1
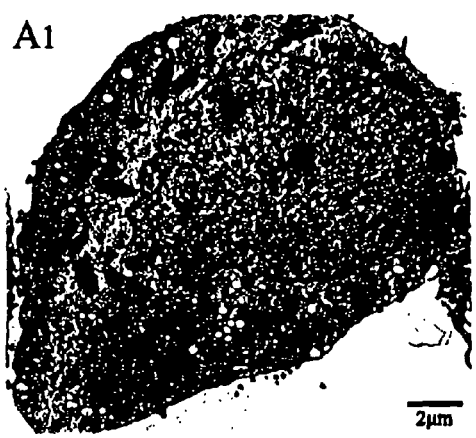
FIG. 12A2
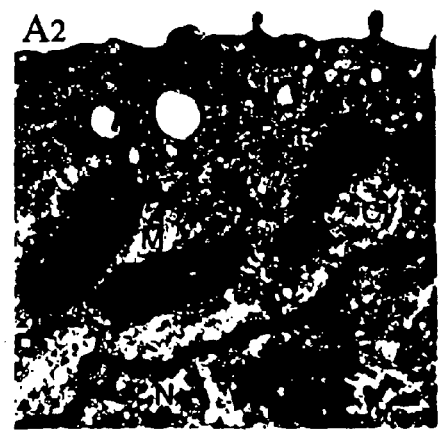
FIG. 12B1
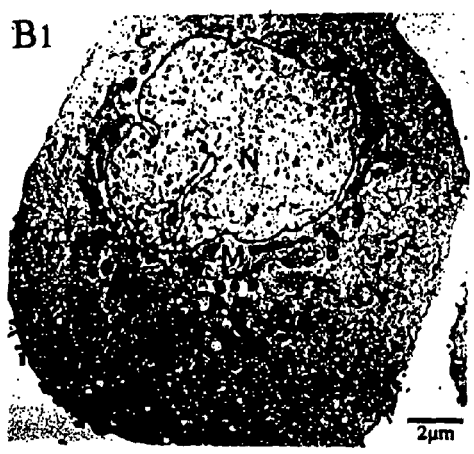
FIG. 12B2
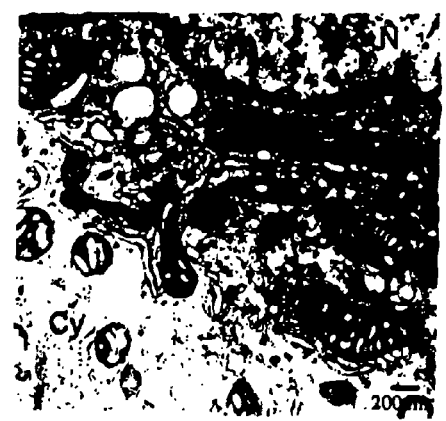

*FIG. 12C1*     *FIG. 12C2*
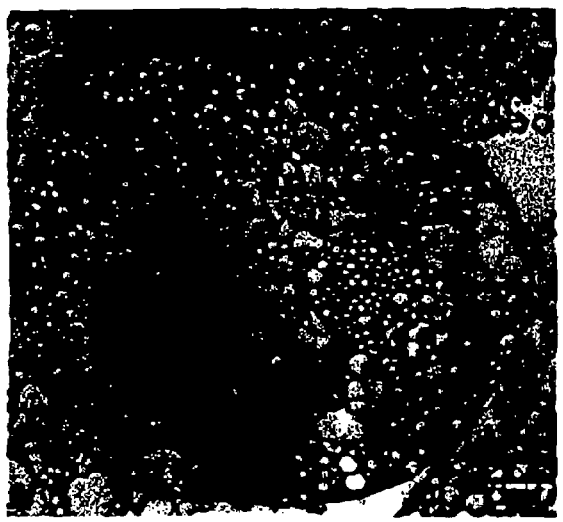
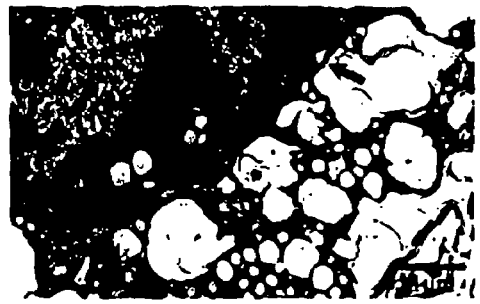
*FIG. 12D*

FIG. 13A
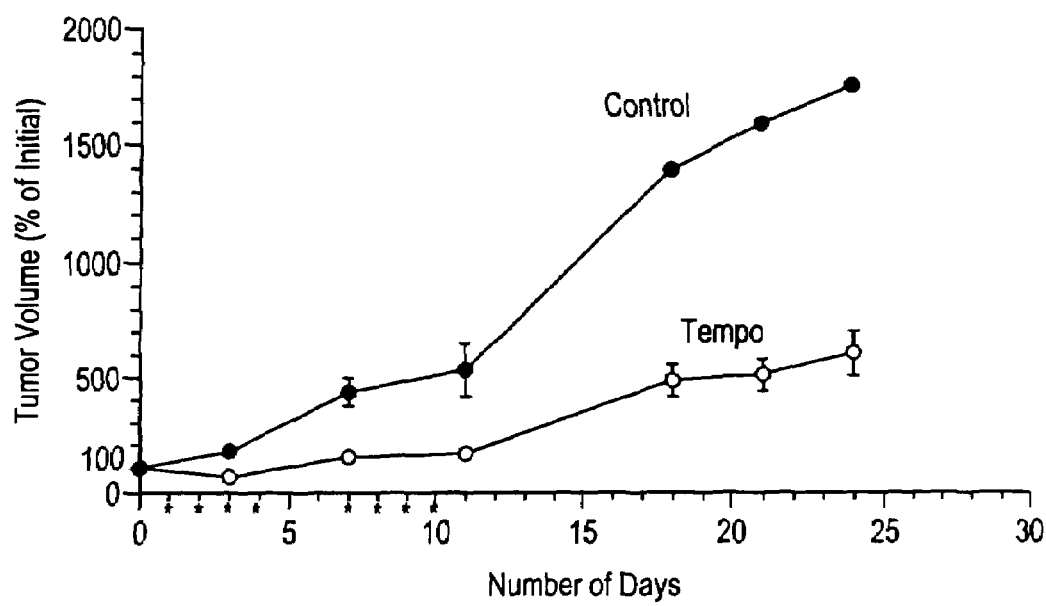
FIG. 13B1
Control
FIG. 13B2
Tempo

COMPOSITIONS AND METHODS FOR INDUCING CELL DEATH

CROSS-REFERENCES TO RELATED APPLICATIONS

This application is a continuation of U.S. patent application Ser. No. 09/720,361, now abandoned, which was filed Jul. 5, 2001, under 35 U.S. §371 as a national stage application of International Patent Application No. PCT/US99/14173, which was filed Jun. 21, 1999, and which claims priority from U.S. Provisional Patent Application No. 60/090,878, filed on Jun. 26, 1998.

Work described herein was funded, in whole or in part, by the National Institutes of Health Grant Nos. CA58984, CA68322 and CA74175. The United States Government may have certain rights in the invention disclosed herein.

FIELD OF THE INVENTION

This invention relates to compositions and methods for inducing cell death, and treatment of diseases and conditions where cell death is beneficial.

INTRODUCTION

A cellular antioxidant defense system composed of enzymes such as catalase, superoxide dismutase, glutathione peroxidase, and glutathione protects cells against toxic oxygen metabolites. Exogenously added free radical scavengers have also been shown to alleviate the deleterious effects of oxygen free radicals (van Asbeck, B. S. et al., 1985, *Science* 227, 756–759; Halliwell, B. 1989, *Free Radical Biol. Med.* 7, 645–651; Myers, M. L. et al., 1985, *Circulation* 72, 915–921; Quintanilha, A. T. and Packer, L., 1977, *Proc. Natl. Acad. Sci. U.S.A.* 74, 570–574). Nitroxide compounds, including tempol and tempo (FIG. 1), are low molecular weight, membrane permeable, stable free radicals that are electron paramagnetic resonance detectable (Berliner, L. J., 1976 *Spin Labeling: Theory and Application*, Academic Press, New York) and have been used classically as probes for biophysical and biochemical processes; they have been used as paramagnetic contrast agents in NMR imaging (Bennett, H. F. et al., 1987, *Magn. Reson. Med.* 4, 93–111; Bennett, H. F. et al., 1987, *Invest. Radiol.* 22, 502–507), as probes for membrane structure (Berliner, L. J. 1979, *Spin Labeling II: Theory and Applications*, Academic Press, New York), and as sensors of oxygen in biological systems (Strzalka, K. et al., 1990, *Arch. Biochem. Biophys* 281: 312–318). However, over the past few years, novel applications of nitroxide have been demonstrated. Nitroxides have been shown to possess antioxidant activity and protect cells against a variety of agents that impose oxidative stress, including superoxide, hydrogen peroxide, and ionizing radiation (Mitchell, J. B. et al. 1990, *Biochemistry* 29, 2802–2807; Smuni, A. et al., 1990, *Adv. Exp. Med. Biol.* 264, 85–92; Samuni, A. et al., 1990, *Free Radical Res. Commun.* 9, 241–249; Mitchell, J. B. et al., 1991, *Arch. Biochem. Biophys.* 289, 62–70; Samuni, A. et al., 1991, *Biochemistry* 30, 555–561; Hahn, S. M. et al., 1992, *Cancer Res.* 52, 1750–1753; Hahn, S. M. et al., 1992, *Radiat. Res.* 132, 87–93; Hahn, S. M. et al. 1995, *Can. J. Physiol. Pharmacol.* 73, 399–403; Samuni, A. et al., 1991, *J. Clin. Invest.* 87, 1526–1530; Gelvan, D. et al., 1991, *Proc. Natl. Acad. Sci. U.S.A.* 88, 4680–4684; Goffman, T. et al., 1992, *Int. J. Radiat. Oncol. Biol. Phys.* 22, 803–806). A variety of chemical mechanisms have been proposed to account for nitroxide antioxidant activity, including superoxide dismutase mimic activity (Samuni, A. et al., 1988, *J. Biol. Chem.* 263, 17921–17924), oxidation of reduced metals that would otherwise catalyze the formation of hydroxyl radicals (Krishna, M. C. et al., 1996, *J. Biol. Chem.* 271, 26018–26025), radical—radical interactions (Mitchell et al., 1990, supra). Although significant research has been conducted at the whole cell level and in animals with nitroxides, little is known at the molecular level of how this novel class of antioxidants affects signal transduction pathways.

Members of the mitogen-activated protein kinase (MAPK) family, including extracellular signal-regulated kinase (ERKs) (p42/44 MAPKs), the stress-activated protein kinases (SAPKs) (also called c-Jun NH2-terminal kinases (p46/54 JNKs/SAPK1)), and p38 MAPK (also termed reactivating kinase (p38RK)), are activated in response to a variety of cellular stresses, such as changes in osmolarity and metabolism, DNA damage, heat shock, ischemia, UV radiation, ionizing radiation, or inflammatory cytokines (Cuenda, A. et al, 1995, *FEBS Lett.* 364, 229–233; Beyaert, R. t al., 1996, *EMBO J.* 15, 1914–1923; Bogoyevitch, M. A. et al., 1996, *Circ. Res.* 79, 162–173; Verheij, C. et al., 1996, *Nature* 380, 75–79; Mendelson, K. G. et al., 1996, *Proc. Natl. Acad. Sci. U.S.A.* 93, 12908–12913; Rosette, C. and Karin, M. 1996, *Science* 274, 1194–1197; Kasid, U. et al., 1996, *Nature* 382, 813–816; Wu, J. et al., 1994, in *Insulin Action, Effects on Gene Expression and Regulation and Glucose Transport* (Draznin, B. and Le Roith, D., eds) pp. 151–177, Humana Press, Totwa, N.J.; Xia, Z. et al, 1995, *Science* 270, 1326–1331; Kyriakis, J. M., and Avruch, J. 12996, *J. Biol. Chem.* 271, 24313–24316; Devary, Y. et al., 1992, *Cell* 71, 1081–1091; Derijard, B. et al., 1995, *Science* 267, 682–685; Sanchez, I. et al., 1994, *Nature* 372, 794–798; Hannun, Y., 1994, *J. Biol. Chem.* 269, 3125–3128; Kharbanda, S. et al., 1995, *Nature* 376, 785–788; Johnson, N. L. et al., 1996, *J. Biol. Chem.* 271, 3229–3237; Hibi, M. et al., 1993, *Genes Dev.* 7, 2135–2148; Kyriakis, J. M. et al., 1994, *Nature* 369, 156–160; Minden, A. et al., 1994, *Science* 266, 1719–1723; Pombo, C. M. et al., 1994, *J. Biol. Chem.* 269, 26546–26551; Suy, S. et al., 1997, *Oncogene* 15, 53–61; Westwick, J. K. et al., 1995, *J. Biol. Chem.* 270, 22689–22692). In many of these instances, free radicals and derivatives play an important role in initiating a cellular signal transduction response (Lander, H. M., 1997, *FASEB J.* 11, 118–124). Unlike the ERK signaling pathway, which primarily promotes growth and proliferation/survival, the SAPK and p38 MAPK pathways result in growth arrest and apoptotic or necrotic cell death. Because nitroxides protect against diverse oxidative insults and may have utility in clinical biomedical research, we have investigated the effects of tempol and tempo on MAPK signal transduction pathways in an attempt to better understand their mechanism of action. Evidence presented here demonstrates that tempol and tempo stimulate distinct pathways of the MAPK signaling cascade. Tempol stimulated the ERK activity and was noncytotoxic, whereas tempo induced ceramide generation, SAPK/JNK activation, and apoptotic death of MDA-MB231 human breast cancer cells. The cytotoxic effect of tempo was also observed in other cancer cell types, PCI-04A laryngeal squamous carcinoma cells, androgen-independent (DU145, PC-3) and androgen-dependent (LNCaP) prostate cancer cell lines. Tempo caused activation of caspase-3, a protease known to cause apoptosis and chromatin fragmentation as evidenced by electron microscopy of LNCap cells. In addition, tempo-treatment caused tumor growth control of MDA-MB231 breast tumor xenografts in athymic mice, suggesting a therapeutic application of tempo or any of its derivatives or formulations.

SUMMARY OF THE INVENTION

This invention describes tempo for use in inducing cell death. tempo has been used previously to protect cells from oxidative damage. The cytotoxic effect of tempo described in this application is both novel and unexpected.

Therefore, one object of the present invention is to provide a method for inducing cell death by introducing to said cell, tissue, or tumor mass a composition containing tempo or a functional derivative of tempo such that cell death is induced.

It is another object of the present invention to provide a composition comprising tempo for inducing cell death and as a therapeutic composition alone or in combination with other anticancer agents for the treatment of cancer.

It is yet another object of the present invention to provide a method for the treatment of cancer by administering to a patient a composition comprising tempo as described above, for example, a liposomal formulation of tempo.

BRIEF DESCRIPTION OF THE DRAWINGS

These and other features, aspects, and advantages of the present invention will become better understood with reference to the following description, appended claims, and accompanying drawings where:

FIGS. 3A, 3B1, 3B2. Tempol and tempo stimulate tyrosine phosphorylation and enzymatic activity of Raf-1 protein kinase in vivo. 3A, Cells were grown in serum-free medium overnight and treated with tempol (10 mM) or tempo (10 mM) for 15 minutes and lysed. Normalized protein contents (1 mg) were immunoprecipitated (IP) with agarose-conjugated anti-Raf-1 polyclonal antibody, followed by immunoblotting (IB) with anti-PY Mab (top). The same blot was stripped and reprobed with anti-Raf-1 Mab (bottom). Data shown is representative from 2–3 independent experiments. UT, untreated cells grown in serum-free medium, and treated with 1% ethanol. 3B1, 3B2, Raf-1 protein kinase activity was measured either by a kinase cascade A "read-out" assay 3B1, or using the Syntide 2 phosphorylation assay 3B2. Cells were grown in serum-free medium overnight, followed by treatment with tempol (10 mM) or tempo (10 mM) for indicated times and lysis. WCLs (1 mg) were immunoprecipitated with agarose-conjugated anti-Raf-1 antibody. For the coupled-kinase cascade reaction, Raf-1 immune-complexes were first incubated at 30° C. for 30 min with 5 nmol of $[\gamma^{32}P]$-ATP, inactive MAPK kinase (0.4 ug), and inactive MAPK (1 ug) in 40 ml kinase reaction buffer. MBP (20 ug) was then added to the first reaction mixture (8 ul) and reaction continued at 30° C. for 10 min in 30 ul kinase reaction buffer. MBP phosphorylation was quantified using a filter binding assay as described in materials and methods. For the Syntide 2 phosphorylation assay, Raf-1 immune-complexes were incubated at 30° C. for 20 min with 5 mmol of $[\gamma^{32}P]$-ATP and 5 ug of Syntide-2 in 40 ul kinase reaction buffer, and Syntide-2 phosphorylation was quantified using a filter binding assay. Data shown are mean±standard deviation (s.d.) from 2–3 independent experiments. Control, cells were grown overnight in serum-free medium and treated with 1% ethanol for 1 h (top) or 2 h (bottom).

FIGS. 4A, 4B. Tempol stimulates ERK1 activity. Cells were grown in serum-free medium overnight, treated with tempol (10 mM) or tempo (10 mM) for 2 h and lysed. WCL (1 mg) were immunoprecipitated with agarose-conjugated anti-ERK1 antibody, and in vitro MBP phosphorylation assay was performed as described in experimental procedures. The incorporation of $\gamma^{32}P$ into MBP was determined in a filter binding assay 4A. In other independent experiments, the reaction products were electrophoresed on 15% SDS-PAGE and MBP (at ~18 kDa) was visualized by autoradiography 4B. Cont/Control, cells grown overnight in serum-free medium, and treated with 1% ethanol for 2 h.

FIGS. 5A, 5B, 5C. Tempo stimulates tyrosine phosphorylation and activity of SAPK. Cells were grown in serum-free medium overnight, and treated with tempol (10 mM) or tempo (10 mM) for indicated times, followed by lysis. 5A. WCLs (1 mg) were immunoprecipitated with agarose-conjugated anti-SAPK antibody, followed by immunoblotting with anti-PY MAb. 5B. In other independent experiments, anti-SAPK immunoprecipitates were first probed with anti-PY MAb (top), and the blot was then reprobed with anti-SAPK antibody (bottom). 5C. Cells were grown in serum-free medium overnight and treated with tempol (10 mM) or tempo (10 mM) for 2 h. WCLs were immunoprecipitated with anti-JNK1 antibody, and the JNK1 activity in immunoprecipitates was measured using GST-cJun (~41 kDa) as a substrate. UT, untreated cells grown overnight in serum-free medium; CONT/Control, cells grown in serum-free medium overnight, and treated with 1% ethanol for 2 h.

FIGS. (7A1–7A3), (7B1–7B2), (7C1–7C3), (7D1–7D2), (7E1–7E3), (7F1–7F2). Tempo induces apoptotic cell death. Cells were grown in serum-free medium overnight in T-25 flasks and treated with tempol (10 mM) or tempo (10 mM) for various times, trypsinized, and then resuspended in 200 ul 1× binding buffer as described in experimental procedures. The cell suspension was double-stained with annexin V-FITC and propidium iodide and analyzed by flow cytometry. Background signal was determined by comparison with double-stained, single-stained, or unstained control cells. (7A1–7A3), (7C1–7C3), and (7E1–7E3) are cytograms showing a relative distribution of viable (V), apoptotic (A), and necrotic (N) cells at 2 h following tempol or tempo treatment of MDA-MB 231 cells (A), PCI-04A cells (C), and PC-3 cells (E). (7B1–7B3), (7D1–7D2), and (7F1–7F2) are time course analyses of MDA-MB 231 cells (B), PCT-04A cells (D), and PC-3 cells (F). 100,000 cells were analyzed at each time point in triplicate (B) or quadruplicate (D and F). Solid bars, 1% ethanol, striped bars, 10 mM tempol, empty bars, 10 mM tempo. (7A1–7A3), The percentage of MDA-MB 231 cells in each quadrant is: Control (7A1)—V, 92.88%, A, 6.05%, N, 1.06%; Tempol (7A2)—V, 92.29%, A, 6.32%, N, 1.31%; Tempo (7A3), V, 35.83%, A, 52.42%, N, 10.90%. Data shown are representative from three to four independent experiments. (7B1–7B2), Time course analysis of MDA-MB 231 cells undergoing apoptosis (annexin V-FITC staining) (7B1), or necrosis (propidium iodide staining) (7B2). Values shown are mean±s.d. of triplicate determinations per time point in each treatment category, and representative of three to four independent experiments. (7C1–7C3), The percentage of PCI-04A cells in each quadrant is: Control (7C1), V, 87.64%, A, 3.42%, N, 8.45%; Tempol (7C2), V, 89.79%, A, 5.44%, N, 4.57%; Tempo (7C3), V, 18.61%, A, 48.35%, N, 31.62%. (7D1–7D2), Time course analysis of PCI-04A cells undergoing apoptosis (annexin V-FITC staining) (7D1), or necrosis (propidium iodide staining) (7D2). Values shown are mean±s.d. of quadruplicate determinations per time point in each treatment category. (7E1–7E3), The percentage of PC-3 cells in each quadrant is: Control (7E1), V, 96.61%, A, 1.12%, N, 1.95%; Tempol (7E2), V, 95.76%, A, 1.20%, N, 2.86%; Tempo (7E3), V, 10.76%, A, 2.57%, N, 83.52%. (7F1–7F2), Time course analysis of PC-3 cells undergoing apoptosis (annexin V-FITC staining) (7F1), or necrosis (propidium iodide staining) (7F2). Values shown are mean±s.d. of quadruplicate determinations per time point in each treatment category. Control/C, cells treated with 1% ethanol for 2 h.

Figure 8:
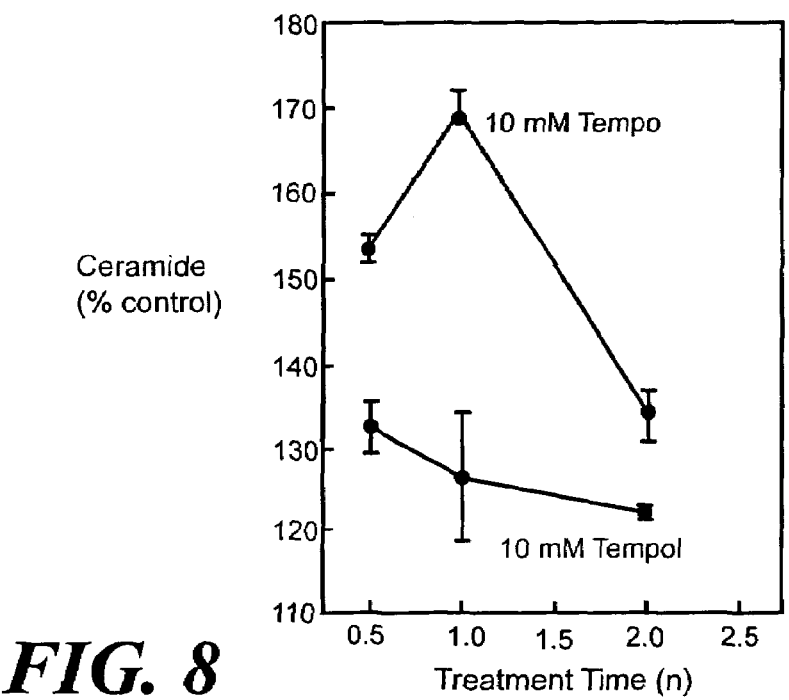

FIG. 8. Ceramide production in tempo-treated MDA-MB 231 cells. Logarithmically growing cells were cultured in serum-free medium overnight in 60 mm dishes, and treated with tempol (10 mM) and tempo (10 mM) for indicated times, followed by lipid extraction, and quantitation of ceramide by DAG kinase assay as described in experimental procedures. The organic phase extract containing the [$\gamma^{32}$P]-labeled ceramide was quantitated. Control cells were grown overnight in serum-free medium, followed by treatment with 1% ethanol for various times ranging from 0.5 h to 2 h. Tempol/tempo treatment values shown are the mean±s.d. of triplicate determinations, the value at each time point normalized to control (100%).

FIGS. (9A1–9A3), (9B1–9B2), (9C1–9C2), (9D1–9D2) shows the time-course and dose-response experiments demonstrating tempo-induced apoptosis in prostate cancer cells (A and B, DU145; C, PC-3; D, LNCaP). Cells were grown overnight in medium containing 10% BCS in T-25 flasks, switched to medium containing 5% BCS and treated with tempo. Following treatment, cells were washed, trypsinized, and resuspended in 200 ml of 1× binding buffer as described before. The cell suspension was double-stained with annexin V-FITC and PI and analyzed by flow cytometry. Background signal was determined by comparison with double stained, single-stained, or unstained control cells. (9A1–9A3): Cytograms of untreated (9A1); 0.1% ethanol-treated (24 hr) (9A2); and tempo-treated DU145 cells (2.5 mM, 24 hr) (9A3). Each panel shows relative distribution of viable (bottom left quadrant), apoptotic (bottom right quadrant), and necrotic cells (top right quadrant). (9B1–9B2), (9C1–9C2), (9D1–9D2): apoptosis (9B1, 9C1, 9D1) and necrosis (9B2, 9C2, 9C3) in cells treated with tempo (B, 2.5 mM; C, 24 hr; D, doses and times as indicated). Values shown are mean q S.D. of triplicate determination per point in each treatment category.

Figure 10:
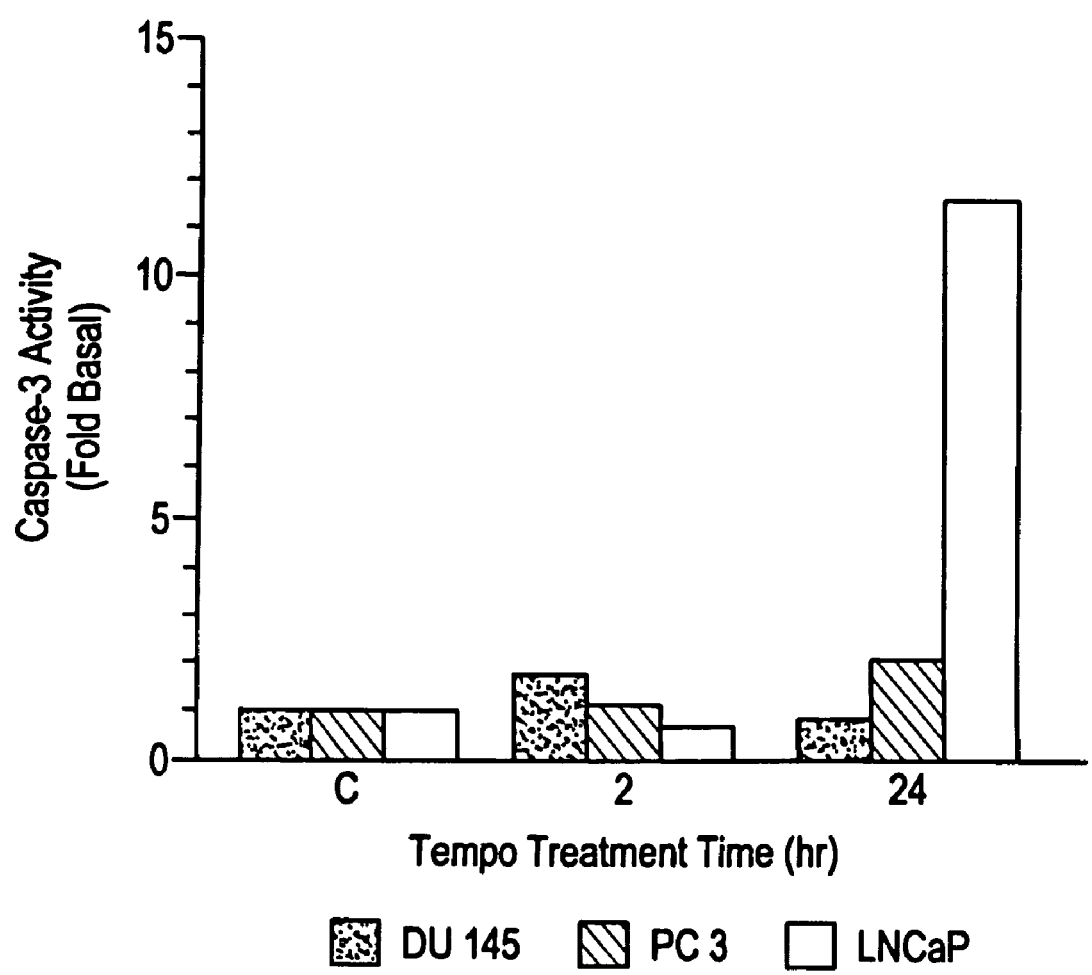

FIG. 10 illustrates the effect of tempo on caspase-3 activity in prostate cancer cell lines. Cells were treated with 2.5 mM tempo for indicated times in duplicate or triplicate as described in legend to FIG. 2. Representative data from one experiment are shown. Experiments was repeated 2–3 times.

FIGS. (11A1–11A2), (11B1–11B2) shows phase contrast light microscopy of LNCaP cells. LNCaP cells (1×106) were seeded in 25 cm2 tissue culture flasks in RPMI medium containing 10% BCS overnight, followed by change to RPMI medium containing 5% BCS stimulation with 0.1% ethanol (control, 11A1, 11B1) or tempo (2.5 mM, 11A2, 11B2) for indicated times.

FIGS. (12A1–12A2), (12B1–12B2), (12C1–12C2), (12D) displays transmission electron microscopy of LNCaP cells. 12A1, untreated, 4,000×; 12A2, a portion of the cell shown in 12A1, 20,000×; 12B1, 0.1% ethanol, 24 hr, 4,000×; 12B2, a portion of the cell shown in 12B1, 20,000×; 12C1, 5 mM tempo, 24 hr, 4,000×; 12C2, a portion of the cell shown in 12C1, 8,0000×; 12D, 5 mM tempo, 24 hr, a portion of another cell, 20,000×. M, mitochondria; G, golgi apparatus; RER, rough endoplasmic reticulum; Cy, cytoplasm; N, nucleus; Arrow in panel C2 indicates swelling in the nuclear membrane.

FIGS. (13A), (13B1–13B2) illustrates the effects of tempo on the growth of human breast tumor xenografts in athymic mice. 13A. Tempo (200 mg/kg) was administered intratumorally once daily for a total of 8 days (*). Control group was treated simultaneously with an equal volume of ethanol (10%). Experiment was terminated when the control tumor volumes exceeded the recommended tumor burden. Each point represents mean q S.E. (n=4). Experiment was repeated twice with comparable results. (13B1–13B2). Representative tumor-bearing mice. Mice were treated with 10% ethanol (13B1) or tempo (13B2) as explained above.

DETAILED DESCRIPTION

Tempo is a stable nitroxide free radical that is shown to have antioxidant catalytic activity which mimics those of superoxide dismutase (SOD), and which when existing in vivo, can interact with other substances to perform catalase-mimic activity. In the past, nitroxides including tempo, have been used in electron spin resonance spectroscopy as "spin labels" for studying conformational and motional characteristics of biomacromolecules. Nitroxides have also been used to detect reactive free radical intermediates because their chemical structure provides a stable unpaired electron with well defined hyperfine interactions. In addition, nitroxides have been observed to act as enzyme mimics; certain low molecular weight nitroxides have been identified to mimic the activity of superoxide dismutase (Samuni, A et al., 1988, *J. Biol. Chem.* 263, 17921) and catalase (Mehlhom, R. J. et al., 1992, *Free Rad. Res. Comm.* 17, 157). Numerous studies also show that nitroxides that are permeable to cell membranes are capable of short-term protection of mammalian cells against cytotoxicity from superoxide anion generated by hypoxanthine/xanthine oxidase and from hydrogen peroxide exposure. The ability of tempo to induce cell death in vitro and in vivo is novel and unexpected. Delivery of tempo to the desired cells can be achieved by conjugating tempo to a marker specific to the desired cells. Such markers include antibodies specific for such cells, growth factors for which the cells have receptors, or ligands which bind specifically to a factor on such cells. For example, Her/2neu ligands are selective for breast cancer cells.

By "tempo" is meant the stable nitroxide free radical, its precursor (such as the N—H form), and derivatives thereof including their corresponding hydroxylamine derivative (N—OH) where the oxygen atoms are replaced with a hydroxyl group and exist in a hydrogen halide form, and the chloride salt form of the hydroxylamine derivative.

By "a functional derivative of tempo" is meant a natural or synthetic substituent, analog or derivative of tempo which retains or contains the cytotoxic effect of tempo. Tempo could be delivered by suitable carriers such as liposomes. Tempo could also be conjugated with target tissue- or cell-specific markers such as antibodies or ligands. In addition, tempo structure could be modified to improve upon its stability in target cells or tissues thereby allowing for a reduced administered concentration of tempo. The formation of substituent, derivatives or synthetic analogs is known in the art and the cytotoxic ability of the compounds generated can be tested by methods known in the art including the assays described in the Examples below.

Tempo has a 6-membered heterocyclic structure in the form of 2,2,6,6-tetramethyl-1-piperidinyloxy, or 2,2,6,6-tetramethylpiperidin-N-oxyl. The substituent groups are usually methyl groups or ethyl groups, although other longer carbon chain species could be used. tempo can be substituted, typically in the 4 position, for example 4-amino, 4-(2-bromoacetamido), 4-(ethoxyfluorophosphonyloxy), 4-(2-iodoacetamido), 4-isothiocyanato, 4-maleimido, 4-(4-nitrobenzoyloxyl), 4-oxo, 4-phosphonooxy, and the like. Other natural or synthetic derivatives and precursors of tempo which result in a compound which effectively induces cell death is part of this invention. Methods, such as those described below and other methods, are known in the art for testing cytotoxicity of a compound. Persons with ordinary skill in the art recognize that by substituting various functional groups on the nitroxide, it is possible to manipulate properties including solubility, biodistribution, in vivo stability, and tolerance.

In this invention is described a method for inducing cell death comprising administering to a cell a composition comprising tempo or a functional derivative of tempo in an amount sufficient to induce death of said cell. The composition may further comprise an excipient or diluent or other medicament or treatment, or a molecule or carrier for the site specific localization of tempo or its functional derivative. A carrier can be a biomolecule or a synthetic molecule such as dextran.

Results from experiments described below indicate that tempo induces cell death by activating the SAPK or caspase-3 signaling cascade. Therefore, another embodiment of the present invention relates to a method for activating the SAPK signaling cascade or a caspase-3 cascade in a cell. The method comprises administering a composition comprising tempo to a cell in an amount effective for activating the SAPK signaling cascade or caspase-3 signaling cascade in said cell.

A variety of techniques have been described to covalently attach a nitroxide to biomolecules, including hemoglobin, albumin, immunoglobulins, and liposomes. See e.g. McConnell et al., 1970, *Quart. Rev. Biophys.* 3, 91; Hamilton et al., 1968, *Structural Chemistry and Molecular Biology*. A Rich et al., eds. W.H. Freeman, San Francisco, p. 115; Griggith et al., 1969, Acc. Chem. REs. 2, 17. Pursuant to this invention, it is possible to select or design carriers which can deliver tempo to particular sites in the body as a means of localizing therapeutic, apoptotic activity. Carriers include, but are not limited to, liposomes since tempo is lipophilic. Targets include, but are not limited to, tumor cells containing specific ligands, receptor molecules, e.g. receptors for growth factors, such as epidermal growth factor, Her-2/New, fibroblast growth factor; or cytokines such as interleukins, interferons, and tumor necrosis factor.

Diseases where selective cell death is beneficial or can be part of the treatment of said disease include diseases associated with abnormal cell proliferation, such as warts, moles, and the like, cancer, e.g. prostate, breast, ovary, head and neck, kidney, lungs, bone, brain, pancreas, liver, or any other disease where diseased cell death is beneficial.

The levels of tempo which may be administered pusuant to this invention are well tolerated in animals and are expected to be well tolerated in humans. For example, a tolerated intraperitoneal dose of tempo in mice is 5 mg/kg to 1000 mg/kg. Intratumoral tolerance can be over 200 mg/kg. Further, if the tempo is bound to a carrier and injected intravenously, the carrier may serve to confine the tempo to the vascular compartment, where the utility is optimized, due to the membrane impermeability of the carrier.

When tempo is injected, it diffuses rapidly into the intracellular space, where it is reduced to the hyroxylamine form from an oxoammonium intermediate. The hydroxylamine does not have the catalytic activity of tempo. The hydroxylamine is chemically stable and relatively persistent in the body and, in accord with the teachings of this invention, can be chemically converted back to the active from of the nitroxide. This in vivo conversion enables the safe clinical use of tempo to provide a sustained activity. When conversion of hydroxylamine is selective, selective cell death is possible.

In addition, this invention describes tempo-containing compounds that are associated with a container for storage or administration of pharmaceuticals such as intravenous fluids, topical agents and others. In view of the stable chemical nature of tempo, compositions containing tempo can be administered by various routes. Tempo can be administered parenterally or orally. In the reduced form, hydroxylamine, can act locally in the gastrointestinal system or be taken up into the blood. Thus, sustained activity can be provided in all body compartments. Tempo complexed to a macromolecule can be administered parenterally where it will remain localized in the extracellular space thereby providing a localized effect.

With respect to selecting a particular formulation and method of administration pursuant to this invention, the formulation and method of administration are dictated by the particular application. The selection of a tempo-based compound is based on the site where activity is desired. Where specific activity is desired in the gastrointestinal tract, a tempo-dextran complex is preferred because such a compound is less susceptible to enzymatic digestion while in the gastrointestinal tract. In such an application, oral or rectal administration is preferred. Where specific activity is sought for the intravenous or intravascular regions, such as the cardiovascular system, a tempo-albumin complex is preferred because albumin is a major plasma protein, is well-tolerated, easy to administer, and exhibits an extended plasma half-life. The same rationale applies for intraperitoneal or intradermal administration. If specific activity in the lungs is desired, an aerosol from of tempo of tempo-albumin complex is preferred. As will be apparent to those skilled in the art, these preferred formulations may be altered depending on the particular application. Tempo can be administered intratumourally. The dosage will depend upon the disease indication and the route of administration but should be between 5–2000 mg/kg of body weight/day. The duration of treatment will extend through the course of the disease symptoms, possibly continuously using a slow-releasing pump or formulation, or single or multiple bolus intratumoral injections. Multiple doses may be required, the number of doses depending upon disease delivery vehicle and efficacy data from clinical trials.

The formulation or method of administration should achieve a systemic or tissue specific distribution commensurate in scope with the extent of the disease or the region to be treated.

The formulations of the invention may also include additional solvents and/or carrier materials and/or extenders such as alcohols, e.g. ethanol, water, sodium chloride or dextrose or other pharmaceutically acceptable solvents used for systemic, including oral or parenteral, administration.

In carrying out the method of the present invention, tempo in combination with the solvent or carrier or optionally an additional pharmaceutical therein, or tempo alone, may be administered to mammalian species, such as monkeys, dogs, cats, rats, humans, etc. Methods of administration include but are not limited to oral, intradermal, transdermal, intravenous, subcutaneous, intramuscular, intraperitoneal, and intranasal routes. Such administration can be done in either bolus or repeat doses or continuously by infusion for instance.

Where tempo alone or in combination with any of the other components of the formulation of the invention is to be administered by angiography or intracoronary injection, it (or the combination) will be formulated in a conventional vehicle, such as distilled water, saline, Ringer's solution, or other conventional carriers.

Tempo alone or in combination with any of the other components of the formulation of the invention may also be incorporated in a conventional dosage form, such as a tablet, capsule or elixir or injectable. The above dosage forms will also include the necessary carrier material, excipient, lubricant, buffer, antibacterial, bulking agent (such as mannitol), anti-oxidants (ascorbic acid of sodium bisulfite) or the like. Parenteral dosage forms are preferred, although oral forms may be satisfactory as well.

A pharmaceutical kit comprising one or more containers filled with one or more of the tempo compositions can be included along with containers containing the solvent or carrier and other necessary reagent or reagents for mixing and dissolving any of the components of the kit.

All documents cited herein supra and infra are hereby incorporated in their entirety by reference thereto.

This invention can be better understood by referring to the following examples which are given for illustrative purposes only and are not meant to limit the invention.

The following MATERIALS AND METHODS were used in the examples that follow.

Antibodies and Reagents—The following antibodies were used in this study: anti-SAPK polyclonal antibody (α-NT), anti-phosphotyrosine monoclonal (MAb) antibody (α-PY, 4G10), and agarose conjugated α-PY (UBI, Lake Placid, N.Y.); agarose conjugated anti-ERK-1 (C-16, sc-93ac), anti-JNK1 (C-17, sc-474ac), and anti-Raf-1 (C-12) polyclonal antibodies (Santa Cruz Biotechnology, Inc., Santa Cruz, Calif.); anti-Raf-1 MAb (c-Raf-1) and anti-ERK-1 MAb (MK12) (Transduction Laboratories, Lexington, Ky.). Protein A-agarose and Syntide-2 were obtained from Santa Cruz Biotechnology, Inc. (Santa Cruz, Calif.). The nitroxide compounds tempo (2,2,6,6-tetramethylpiperidine-N-oxyl) and tempol (4-hydroxy-tempo) were obtained from Aldrich Chemical Co (Milwaukee, Wis.). Sodium dodecyl sulfate polyacrylamide gel electrophoresis (SDS-PAGE) reagents and 5× TGS electrophoretic buffer were purchased from Gibco BRL (Grand Island, N.Y.), and pre-mixed 10× Tris-glycine transfer buffer was obtained BioRad Laboratories (Hercules, Calif.). All other reagents were obtained from Sigma (St. Louis, Mo.) unless otherwise indicated.

Cell Culture, Treatments with Tempol and Tempo, and Preparation of Cell Lysates—MDA-MB 231 human breast cancer cells were grown to near confluence in 75 cm$^2$ tissue culture flasks in Improved Minimum Essential Medium (IMEM) (Cellgro) containing 10% fetal bovine serum (FBS) and 2 mM L-glutamine in a humidified atmosphere of 5% $CO_2$: 95% air at 37° C. Cells were trypsinized and plated into a 150 mm tissue culture dish (two dishes per flask) overnight in medium containing 10% FBS followed by two washes with phosphate buffer saline (PBS). Cultures were maintained in serum-free medium overnight prior to tempol (10 mM) or tempo (10 mM) treatment. Both nitroxide radicals were dissolved in ethanol before use. For the extraction of whole cell lysates (WCL), cells with or without nitroxide treatment were washed three times with ice-cold PBS containing 0.5 uM sodium orthovanadate ($Na_3VO_4$) and lysed in lysis buffer (50 mM HEPES, pH 7.5, 1% Nonidet P-40 (NP-40), 10% glycerol, 4 ug/ml each of leupeptin, aprotinin and pepstatin A, 1 mM $Na_3VO_4$, 1 mM phenylmethylsulfonyl fluoride (PMSF), 25 mM sodium fluoride (NaF), and 0.5 mM EDTA. WCL was agitated for 1 h at 4° C. and centrifuged in a microcentrifuge at 15,000× g, 4° C. for 15 min to remove cellular debris. The supernatant was aliquoted and stored at −70° C. until use.

Immunoprecipitation and Immunoblotting—Whole cell lysate (1 mg) was immunoprecipitated with the appropriate agarose-conjugated antibody (1 ug/ml of lysis buffer) overnight at 4° C. with constant agitation. For SAPK immunoprecipitation, WCL (1 mg) was immunoprecipitated with anti-SAPK antibody (5 ug/ml) overnight followed by addition of protein A-Agarose (50 ul of 250 ul/ml stock) and incubation for 2 h at 4° C. Immune-complex beads were collected by microcentrifugation at 15,000×g for 5 min followed by three washes with lysis buffer. The beads were resuspended in 2× electrophoresis sample buffer, boiled for 5 min, and proteins were resolved by 10% SDS-PAGE and transferred to an Immobilon-P membrane. The membrane was blocked with 4% bovine serum albumin (BSA) in PBS-Tween (0.25%), and immunoblotted with the desired primary antibody at 1:2000, followed by 1:10,000 dilution of an appropriate horseradish peroxidase-coupled secondary antibody. The immunoreactive protein bands were revealed by ECL detection system (Amersham, Arlington Heights, Ill.). The bands of interest were quantified by ImageQuant software version 3.3 (Molecular Dynamics Personal Densitometer, Sunnyvale, Calif.). Prior to reprobing, blots were stripped according to the ECL kit protocol (NEN, Boston, Mass.), as described earlier (Suy, S. et al., 1997, *Oncogene* 15, 53–61).

Raf-1 kinase Assay—Raf-1 protein kinase activity was measured by a kinase cascade assay according to the manufacturer's procedure (UBI, Lake Placid, N.Y.), with the following modifications. Briefly, Raf-1 immune-complex was washed 3 times with lysis buffer and once with kinase binding buffer (KBB) (20 mM MOPS, pH 7.2, 25 mM-glycerol phosphate, 5 mM EGTA, 1 mM $Na_3VO_4$, 1 mM DTT). This was followed by incubation of the immune-complex for 30 min at 30° C. in reaction mixture containing 20 ul of KBB, 10 ul of 0.5 mM ATP/Mg cocktail (75 mM magnesium chloride and 500 uM ATP in KBB), 1.6 ul of inactive MAPK Kinase (0.4 ug) and 4 ul of inactive MAPK (1 ug). At the end of the reaction, 8 ul of the sample mixture was transferred to fresh 1.5 ml microfuge tube, followed by the sequential addition of 10 ul KBB, 10 ul of MBP substrate (2 mg/ml stock), and 10 ul of [γ-$^{32}$P] ATP (1 uCi/ul generated by 1:10 dilution of the stock 3000 Ci/mmole (Dupont NEN, Boston, Mass.) in ATP/Mg$^{2+}$ cocktail). This reaction mixture was incubated for 10 min at 30° C. The immune-complex was then pelleted by brief centrifugation in a bench-top microcentrifuge, and 5 ul of the sample was spotted, in triplicate, onto P81 paper. The radioactive filters were transferred onto a 50 ml conical tube (20 filters per tube) and washed 4 times with 40 ml of 0.75% phosphoric acid (15 min each), followed by a brief acetone wash, and counted using Beckman LS 1801 scintillation counter.

Additionally, the immune-complex-associated Raf-1 activity was measured using Syntide-2 as a substrate. This reaction was initiated by sequential addition of 15 ul KBB, 10 ul of ATP/Mg$^{2+}$ cocktail, 5 ul of Syntide-2 (5 ug), and 10 ul of diluted [γ-$^{32}$P] ATP followed by incubation of the reaction at 30° C. for 20 min. At the end of the incubation, reaction mixture was centrifuged briefly in a bench-top microcentrifuge, and 5 ul of the supernatant was spotted in triplicate onto P81 filter paper, air dried, washed, and counted as described above.

ERK and SAPK/JNK Activities—Whole cell lysates prepared as described above were immunoprecipitated (1 mg) with an agarose conjugated anti-ERK1 antibody or an agarose conjugated anti-JNK1 antibody for 2 h at 4° C. with constant agitation. The immune-complexes were washed 3 times in lysis buffer and once in KBB as mentioned earlier. ERK or JNK activity assay was carried out according to manufacturer's procedures (UBI). Briefly, the ERK1 immunoprecipitates were incubated for 10 min at 30° C. in a kinase reaction containing 10 ul of MBP (myelin basic protein) as substrate (2 mg/ml stock), 10 ul of inhibitor cocktail (20 uM PKC inhibitor peptide, 2 uM protein A inhibitor peptide, and 20 uM compound R24571), and 10 ul of magnesium-ATP cocktail (1·uci [γ-$^{32}$P] ATP generated by 1:10 dilution of stock (3000 Ci/mmol) in 75 mM magnesium chloride and 500 um cold ATP). The immune-complexes were centrifuged briefly in a bench top centrifuge and 5 ul aliquots of the supernatant were spotted in triplicate onto P81 filter papers. The radioactive filters were washed and counted as described above. Alternatively, to visualize the incorporation of [γ-$^{32}$P] into MBP, the kinase reaction was stopped by addition of 2× electrophoresis sample buffer, boiled for 5 min and proteins were resolved by 15% SDS-PAGE, followed by autoradiography. For JNK activity assay, JNK1 immunoprecipitates were incubated for 30 min at 30° C. in 40 ul of kinase reaction mixture containing 10 ul of KBB, 20 ul of the GST-cJun fusion protein (0.2 ug/ul stock), and 10 ul of the diluted [γ-$^{32}$P] ATP as described above. The kinase reaction was stopped with 2× electrophoresis sample buffer, boiled for 5 min, and the supernatant was electrophoresed on a 12.5% SDS-PAGE. The radiolabeled GST-cJun fusion protein was detected by autoradiography.

Cell Viability Assay—Effects of nitroxide compounds on cell viability and proliferation were determined using a cell viability detection kit (4-[3-(4-Iodophenyl)-2-(4-nitrophenyl)-2H-5-tetrazolio]-1,3-benzene disulfonate, WST-1) according to the manufacturer's instructions (Boehringer Mannheim, Indianapolis, Ind.). Briefly, MDA-MB 231 cells were seeded onto 96 well plates at density of 10,000 cells per well and maintained overnight in 10% FBS containing medium. The cells were then washed twice with phosphate buffered saline and re-fed in serum-free medium. The following day, cells were treated for various times with tempol (10 mM) or tempo (10 mM), using six wells per treatment condition. At the end of treatment, medium containing the nitroxide compound was removed and replaced with fresh serum-free medium (100 ul), followed by addition of WST-1 (10 ul). Plates were incubated for 2 h at 37° C. and analyzed at OD=450/600 using a MR 700 microplate reader.

Apoptosis Assay—ApoAlert Annexin V apoptosis detection system (Clontech Lab Inc., Palo Alto, Calif.) was used to measure the relative distribution of apoptotic and necrotic cells. Briefly, cells were seeded at a density of 1×106 cells per 25 cm$^2$ tissue culture flask in medium containing 10% FBS overnight, followed by washing twice in serum-free medium. Cells were maintained overnight in serum-free medium and exposed to tempol (10 mM) or tempo (10 mM) for various times. This was followed by rinsing twice with serum-free medium prior to trypsinization, dilution in two volumes of serum-free medium, and centrifugation at 10,000× g. The cell pellet was washed once with PBS and resuspended in 200 ul of 1× binding buffer. The cell suspension was double-labeled with fluorescein isothiocyanate (FITC)-labeled annexin V (10 ul) and propidium iodide (PI) (10 ul) according to the manufacturer's instructions. Unlabeled cells or untreated cells labeled with either FITC-annexin V or PI, or double-labeled served as internal controls for the background signal. The intensity of the dye uptake by cells was detected using FACStar plus Flow Cytometer (Becton Dickerson, Lincoln Park, N.J.), and data were analyzed using Reproman True Facts software (Seattle, Wash.). Viable cells were FITC−/PI−, apoptotic cells were FITC+/PI−, and necrotic cells were FITC+/PI+.

Ceramide Generation Assay—Ceramide production in MDA-MB 231 cells was determined by diacylglycerol (DAG) kinase assay according to a previously described procedure (Haimovitz-Friedman, A. et al., 1994, *J. Exp. Med.* 180, 525–535; Dressler, K. A. and Kolesnick, R. N., 1990, *J. Biol. Chem.* 265, 14917–14921). Briefly, MDA-MB 231 cells were split (1:2), and after 24 h, the cells were washed twice with PBS and serum-free medium was added, followed by incubation for additional 24 h. The cells (~2× 10$^6$/60 mm dish) were treated with tempo (10 mM) or tempol (10 mM) for various times. Following treatment, floating cells were collected and pelleted by centrifugation for 10 min at 1200 rpm, and attached cells were collected by scraping. Lipids were extracted from all cells (floating and attached) by incubation in 1 ml 100% ice-cold methanol. After a partial purification with chloroform, the extracted lipid in the organic phase was dried under N$_2$ and was treated with a mild alkaline solution (0.1 N KOH in methanol) for 1 h at 37° C. to remove glycerolphospholipids. The organic phase extract was resuspended in 20 ul of 7.5% n-octyl-β-D-glucopyranoside, 5 mM cardiolipin, 1 mM EDTA followed by the addition of 40 ul of purified DAG kinase in DAG kinase buffer (20 mM Tris-HCl (pH 7.4), 10 mM DTT, 1.5 M NaCl, 250 mM sucrose, 15% glycerol). The kinase reaction was initiated by the addition of 20 ul of diluted [γ-$^{32}$P] ATP (10 mM at 1,000 dpm/pmol in DAG kinase buffer) and incubated for 30 min at 22° C. This reaction was terminated by extraction of lipids with 1 ml CHCl$_3$:CH$_3$:OH:HCl (100:100:1), 170 ul buffered saline solution (135 mM NaCl, 1.5 mM CaCl$_2$, 0.5 mM MgCl$_2$, 5.6 mM glucose, and 10 mM HEPES, pH 7.2), and 30 ul of 100 mM EDTA. The lower organic phase containing ceramide-1-phosphate was collected and dried under N$_2$ followed by spotting and run of 40 ul (80%) onto a thin layer chromatographic (TLC) (Whatman silica gel 150A) plate, and developing in chamber containing CHCl$_3$:CH$_3$OH:HAc (65:15:5, vol/vol) as solvent. The spot containing the ceramide-1-phosphate was visualized by autoradiography, and the incorporated $^{32}$P was removed by scraping, and quantified by Cerenkov counting. A standard curve consisting of known amount of ceramide was used as a comparison to the level of observed ceramide generated in MDA-MB 231 cells.

Caspase-3 activity assay:

ApoAlert CPP32 activity/caspase-3 assay kit was used to measure caspase-3 activity in cells according to manufacturer's instructions (Clontech). Briefly, after tempo treatment, cells were washed 3 times with ice-cold PBS and lysed in Clontech cell lysis buffer for 10 min on ice followed by microcentrifugation at 15,000× g for 5 min. Whole cell lysate (50 ug) was incubated for 1 h at 37° C. in caspase-3 reaction mixture containing 10 mM DTT in 2× reaction buffer, 50 uM CPP32 substrate, DEVD-AFC. The amounts of 7-amino-4 trifluoromethyl coumarin (AFC) released were detected by spectrofluorometer (Hitachi F4500) with excitation at 400 nm and emission at 505 nm.

Figure 2:
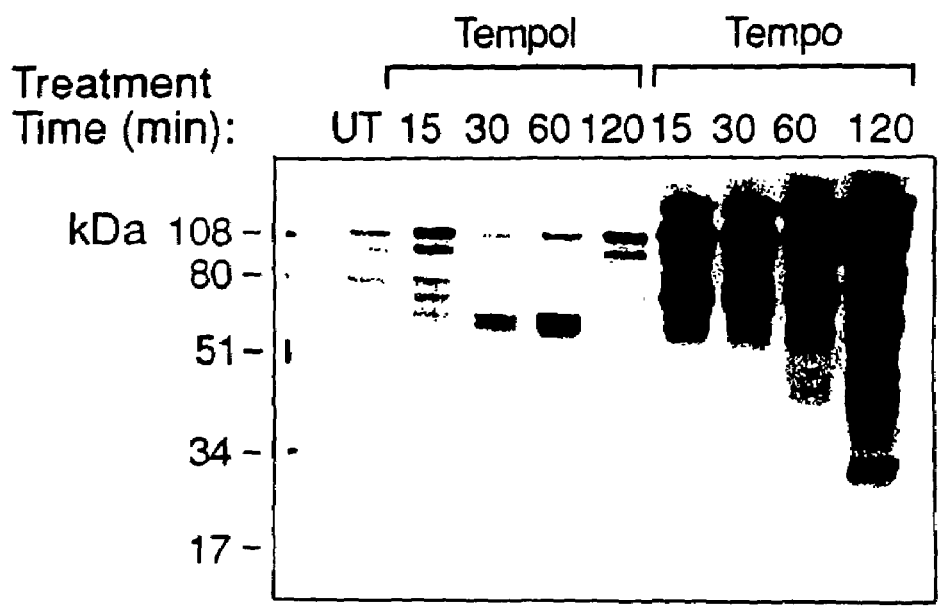
FIG. 2. Effects of tempol and tempo on protein tyrosine phosphorylation. Subconfluent cultures were grown in serum-free medium overnight, followed by treatment with tempol (10 mM) or tempo (10 mM) for indicated times and lysis. Normalized protein contents (1 mg) were immunoprecipitated with agarose-conjugated anti-PY MAb, and then immunoblotted with anti-PY MAb. Data shown is representative of two independent experiments. UT, untreated cells grown overnight in serum-free medium.

Transmission electron microscopy:

LNCaP cells were treated with tempo as described in legend to FIG. 2. Following treatment, monolayer cells were washed three times with PBS, and fixed in 2.5% glutaraldehyde/3% paraformaldehyde in PBS. After fixation, the cell monolayer was washed in PBS. The cells were collected by gentle scraping using a rubber policeman, and centrifuged. The pellet was embedded in 1% agarose to facilitate handling. Post-fixation was performed in 1% osmium tetroxide in distilled water for 1 hr, followed by washing three times in distilled water, enbloc staining with 2% uranyl acetate for 30 min in dark, and washing three times in distilled water. This was followed by processing for conventional ultrathin section electron microscopy. Sections were mounted on 200 mesh-nickle grids, post-stained with lead citrate, and photographed with a JEOL 1200EX-transmission electron microscope operated at 60 kV.

Tumor growth studies:

MDA-MB231 cells (1×10$^6$) were inoculated subcutaneously in the right flank of 4–6 week-old female athymic mice. Tumor growth was monitored biweekly. Mice bearing tumor volumes in the range of 80–100 mm$^3$ were randomly selected for treatment. Tempo treatment was initiated (50 mg/kg–200 mg/kg, intratumoral, once daily, for a total of 8 days), and tumor volumes were measured for a total 25 days from the start of treatment.

EXAMPLE 1

Effects of Tempol and Tempo on Protein Tyrosine Phosphorylation

FIG. 2 illustrates a conspicuous increase in the tyrosine phosphorylation of several as-yet unidentified protein bands within 15 min after the exposure of MDA-MB 231 cells to 10 mM tempo. These levels remained elevated for the duration of the study (2 h). In parallel experiments, minimal protein tyrosine phosphorylation was observed at various times (15 min to 2 h) following the treatment of cells with an equimolar concentration of tempol. These data show that while both nitroxides induced protein tyrosine phosphorylation, the magnitude of this response was clearly higher in tempo-treated cells.

EXAMPLE 2

Figure 1:
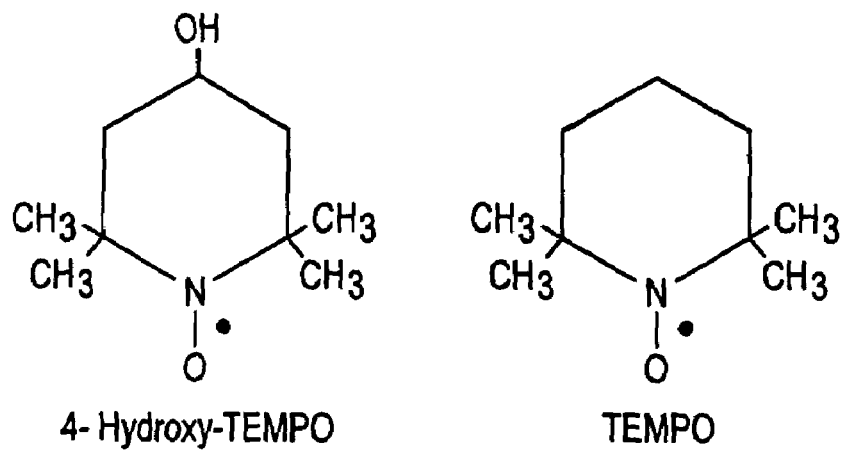
FIG. 1. is a schematic representation of the chemical structures of nitroxide compounds tempol (4-hydroxy-tempo) and tempo.

Tempol and Tempo Stimulate Tyrosine Phosphorylation and Activity of Raf-1 In Vivo Previously we demonstrated that ionizing radiation, a well known stress inducing agent, causes tyrosine phosphorylation of Raf-1 in MDA-MB 231 breast cancer cells (Suy, S. et al., 1997, supra). Here we examined the possibility of tyrosine phosphorylation and activation of Raf-1 protein kinase in response to tempol or tempo. Interestingly, both tempol and tempo treatments led to an increase in the level of tyrosine phosphorylated Raf-1 (Raf$^P$) (FIG. 3A, top panel). The level of total Raf-1 protein remained unchanged (FIG. 3A, bottom panel). The immunoreactive RafP bands were quantified. Densitometric analysis indicated that increase in the level of RafP detected at 15 min was ~5–8 fold, and Raf$^P$ content was comparable to the basal level by 60 min to 120 min (data not shown). The activity of Raf-1 protein kinase was determined by a kinase cascade assay or by the Syntide-2 phosphorylation assay (FIGS. 3B1, 3B2). In agreement with the enhanced tyrosine phosphorylation of Raf-1, tempol or tempo treatment resulted in ~2–3 fold increase in the Raf-1 protein kinase activity.

EXAMPLE 3

Tempol Stimulates ERK Activity

Since Raf-1 activation, generally, leads to ERK (p42/44 MAPK) activation, we examined the effects of tempol and tempo on ERK1 enzymatic activity. Representative experiments are shown in FIGS. 4A and 4B. Approximately 3-fold increase in the enzymatic activity of ERK1 was detected by 2 h in cells treated with tempol (FIG. 4A). Interestingly, however, no change in ERK1 activity was noted following tempo treatment compared with control cells (FIG. 4A). In addition, ERK1 phosphorylation was seen as a shift to a more slowly migrating phosphorylated form (ERK1$^P$) on immunoblots using ERK1 immunoprecipitates at 2 h after tempol exposure (10 mM), but we were unable to identify a shift in the mobility of ERK1 is tempo-treated cells (data not shown).

EXAMPLE 4

Figure 5C:
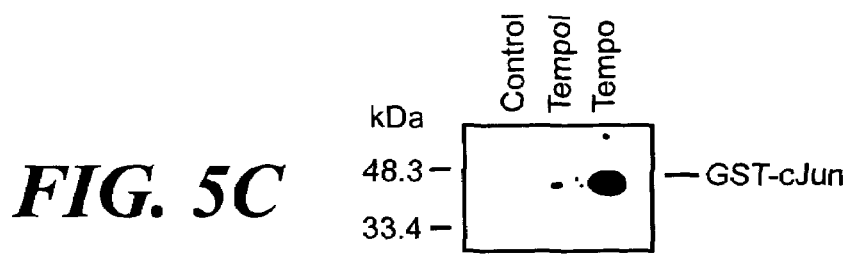

Tempo Treatment Results in Enhanced Phosphorylation and Activation of SAPK In Vivo We next measured the effects of tempol and tempo on SAPK/JNK, a well-known component of the stress-induced signal transduction pathway. The time course experiments indicated that tempo treatment resulted in a significant increase in the level of phosphorylated SAPK (~54 kDa, SAPK$^P$) compared to tempol treatment or untreated controls (FIGS. 5A and 5B). Consistent with these data, SAPK enzymatic activity was significantly induced in tempo-treated cells as shown by the level of phosphorylated GST-cJun (FIG. 5C). Densitometric analysis of three independently performed experiments indicated a 3–7 fold increase in the phosphorylated GST-cJun fusion protein detectable after tempo exposure (10 mM, 2 h) compared to tempol (10 mM, 2 h) or control (1% ethanol, 2 h) treatment.

EXAMPLE 5

Tempo Induces Apoptotic Cell Death

Figure 6:
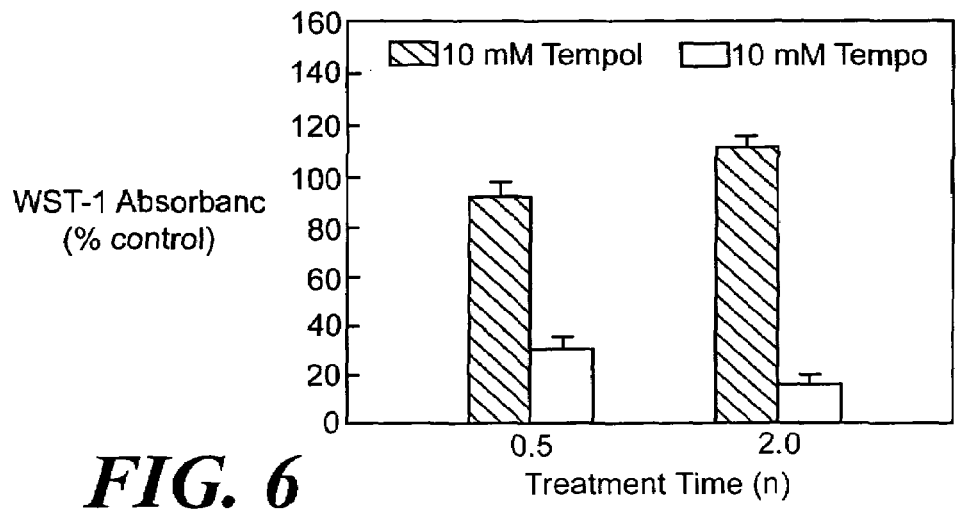
FIG. 6. Effects of tempol and tempo on cell viability. Cells were grown in serum-free medium overnight in 96-well plates, and treated with tempol (10 mM) or tempo (10 mM) for indicated times, followed by removal of medium containing the nitroxide compound. Control cells were grown overnight in serum-free medium, followed by treatment with 1% ethanol for various times. Fresh serum-free medium (100 ul) was added to each well in all plates, including controls followed by the addition of WST-1 (10 ul). Plates were incubated for 2 h at 37° C. and the color solution developed by WST-1 was quantified using a MR 700 microplate reader at OD=450/600. Values shown are mean±s.d. of 6 determinations per treatment condition in a representative experiment, and the experiment was repeated three times.

Several studies have reported that activation of the SAPK signaling cascade is associated with induction of apoptotic cell death (Kyriakis, J. M. and Avruch, J., 1996, supra). To examine the possible cytotoxic effects of tempo, we first used a colorimetric assay to determine the cell viability and proliferation. Treatment of cells with 10 mM tempo resulted in >50% decrease in the number of viable cells within 2 h. In parallel experiments, the number of viable cells in cultures treated with 10 mM tempol was comparable to control cells treated with 1% ethanol (FIG. 6). These observations prompted us to evaluate whether decrease in the number of viable cells following tempo treatment was due to apoptotic and/or necrotic cell death.

Apoptosis is a process of cell death characterized by cytoplasmic shrinkage, nuclear condensation, and DNA fragmentation (Kerr, J. F. R., et al., 1972, *Br. J. Cancer* 26, 239–257). Several reports suggest that an early event leading to apoptosis is accompanied by a loss of cell membrane phospholipid asymmetry as a result of translocation of phosphatidylserine (PS) from the intracellular membrane to the extracellular membrane while leaving the cell membrane intact (Fadok, V. A. et al., 1992, *J. Immunol.* 148, 2207–2216). A PS-binding protein, annexin V, has been used a specific probe to detect externalization of this phospholipid in a variety of murine and human cell types undergoing apoptosis (Martin, S. J., et al., 1995, *J. Exp. Med.* 182, 1545–1556; Koopman, G. et al., 1994, *Blood* 84, 1415–1420). Cell necrosis, on the other hand, is associated with both the translocation of PS to the external cell surface as well as the loss of membrane integrity (Vermes, I. et al., 1995, *J. Immunol. Methods* 184, 39–51). The cell membrane integrity of apoptotic cells can be established with a dye exclusion test using propidium iodide (PI). In the following experiments, we used FITC-conjugated annexin V and propidium iodide (PI) as markers for the evaluation of apoptosis and necrosis. MDA-MB 231 cells treated with tempol or tempo were double-labeled with FITC-conjugated annexin V and propidium iodine (PI) and then subjected to flow cytometric analysis. Representative cytogram analysis of MDA-MB 231 cells with or without nitroxide compound is shown in FIGS. 7A1, 7A2, 7A3. The lower left quadrant represents viable cells (V) which were negative for annexin V and PI. The lower right quadrant represents apoptotic cells (A) which were positive for annexin V staining. The upper right quadrant represents necrotic cells (N) which were positive for both annexin V and PI stains. Tempo treatment (10 mM, 2 h) resulted in a significant increase in both the annexin V uptake (52.42% apoptotic cells) and the annexin V plus PI uptake (10.90% necrotic cells) compared to tempol (10 mM, 2 h) (6.32% apoptotic cells, 1.31% necrotic cells) and control cells (1% ethanol, 2 h) (6.05% apoptotic cells, 1.06% necrotic cells). Time course analysis indicated that tempo treatment resulted in a steady increase in the number of apoptotic cells for upto 2 h, followed by a considerable increase in the number of necrotic cells by 3 h (FIGS. 7B1, 7B2). Tempol treatment did not induce apoptosis or necrosis for the duration of the study (3 h) (FIGS. 7B1, 7B2). These data suggest that tempo-stimulated SAPK phosphorylation and activation may be associated with apoptotic cell death in MDA-MB 231 cells.

To determined the generality of the cytotoxic effect of tempo in cancer cells, we have examined two other cancer cell lines: PCI-04A, a human laryngeal squamous carcinoma-derived cell line (Heo, D. S. et al., 1989, *Cancer Res.* 49, 5167–5175), and PC-3, a human prostate cancer cell line. The data shown in FIGS. 7C1, 7C2, 7C3 and 7D1, 7D2 demonstrate a significant level of apoptosis and necrosis at 2 h post-tempo treatment (10 mM) in PCI-04A cells. In PC-3 cells, 10 mM tempo treatment resulted in ~84% necrotic cells by 2 h, implying that this treatment condition was highly toxic (FIGS. 7E1, 7E2, 7E3 and 7F1, 7F2). Tempo also induced apoptotic cell death in bovine aortic endothelial cells, as measured by the bisbenzamide trihydrochloride/Hoechst-33258 staining method, as previously described (Haimovitz-Friedman, A. et al., 1994, *J. Exp. Med.* 180, 525–535) (control: 4 h, 1.55±0.02%; 8 h, 1.99±0.43%; tempo (5 mM): 4 h, 3.97±0.33%; 8 h, 38.85±1.69%) (Suy, S. et al., 1998, *J. Biol. Chem.* These results clearly demonstrate that tempo but not tempol induces cell death in different types of cancer cells.

EXAMPLE 6

Ceramide Generation in Tempo-treated MDA-MB 231 cells—Ceramide, a second messenger molecule generated as a result of hydrolysis of the plasma membrane phospholipid sphingomyelin or via de novo synthesis, has been implicated in a variety of biological responses to environmental cues (Kolesnick, R. N., 1992, *Trends Cell Biol.* 2, 232). Increase in ceramide has been correlated with increased JNK/SAPK activity, and ceramide and SAPK/JNK have been shown to participate in a signal transduction pathway leading to cell death (Verheij, C. et al., 1996, supra; Westwick, J. K. et al., 1995, supra; Yan, M. et al., 1994, *Nature* 372, 798–800; Zanke, B. W. et al., 1996, *Curr. Biol.* 6, 606–613). To assess the possibility of a role of ceramide in tempo-induced SAPK and apoptosis, we used a DAG kinase assay to quantify the ceramide levels in MDA-MD 231 cells treated with or without the nitroxide compound. A 54% increase over control (normalized to 100%) in ceramide level was observed at 30 min, and ceramide level reached 71% over control at 1 h post-tempo treatment (FIG. 8). The level of ceramide generated in tempol-treated cells was not significantly higher compared to control cells at all time points. Ceramide production preceded maximal stimulation of JNK/SAPK and apoptosis, implying its involvement in tempo-induced signaling in MDA-MB 231 cells.

EXAMPLE 7

To investigate tempo's effect on prostate cancer cells, human androgen-independent prostate cancer-derived cell lines (DU145 and PC3) were grown to near confluence in 75 cm$^2$-tissue flasks in Improved Minimum Essential Medium (IMEM) (Cellgro) containing 10% bovine calf serum (BCS) supplemented with 2 mM L-glutamine and 200 IU/ml penicillin and streptomycin mixture in a humidified atmosphere of 5% $CO_2$:95% air at 37° C. Human androgen-dependent prostate cancer-derived cell line (LNCaP) was cultured in RPMI 1640 medium containing 10% BCS and 2 mM L-glutamine. Cells were trypsinized and seeded in equal numbers overnight in 150 mm$^2$ tissue culture dishes (two dishes per flask) or 25 cm$^2$ flasks (1×10$^6$ cells per flask). Cells were treated in medium containing 5% BCS with desired concentration of tempo for various times. Tempo was dissolved in ethanol (0.1%) before use. Control cultures were treated with ethanol (0.1%) for various times. Following treatment, cells were washed 3 times with PBS. ApoAlert Annexin V apoptosis detection system (Clontech) was used to measure the relative distribution of apoptotic and necrotic cells in response to tempo as described earlier. Results of flow cytometric analysis of cells labeled with FITC-conjugated annexin V or propidium iodide showed that tempo treatment led to significant levels of apoptosis in these prostate tumor cell lines. In DU145 cells and PC-3 cells, 2.5 mM tempo treatment for 24 hr resulted in approximately 3.4-fold and 6.7-fold increases in the number of apoptotic cells, respectively. In LNCaP cells, a relatively higher level of apoptosis was observed (1 mM tempo, 24 hr, approximately 12-fold; 5 mM, 4 hr, approximately 15-fold) (FIGS. 9A1, 9A2, 9A3, 9B1, 9B2, 9C1, 9C2, 9D1, 9D2).

EXAMPLE 8

Activation of the caspase family of cysteine proteases is an important molecular hallmark of programmed cell death. Caspase-3 is a well known downstream effector of apoptotic signal transduction pathway induced by a variety of agents. We asked whether tempo activates caspase-3 activity in prostate cancer cells. As shown in FIG. 10, tempo induced the activation of caspase-3, albeit to varying levels in different prostate cancer cell lines. In DU145 and PC3 cells, only modest increases in the level of caspase-3 activity were observed with tempo (2.5 mM) (DU145, 2 hr, ~170%; PC3, 24 hr, ~200%). Consistent with a significant tempo-induced apoptosis in LNCaP cells, ~12-fold increase in caspase activity was noted in tempo-treated LNCaP cells (2.5 mM, 24 hr).

EXAMPLE 9

At the light microscopic level, a distinct change in cell morphology from spindle shaped, highly refractile appearance to a more flattened appearance was noticed after tempo treatment of LNCaP cells (FIGS. 11A1, 11A2, 11B1, 11B2).

EXAMPLE 10

We then undertook the ultrastructural analysis to examine if tempo induces the morphological features of apoptosis. Electron microscopy revealed aggregation and marginalization of chromatin in the nuclei of a large number of tempo-treated LNCaP cells. The nuclear envelope remained essentially intact. In the cytoplasm, the golgi apparatus and rough endoplasmic reticulum had disappeared or disrupted, and mitochondria were not discernible in a majority of tempo-treated cells. Interestingly, mitochondria in 0.1% ethanol-treated cells were swollen compared to the untreated controls. Pronounced vacuolation, perhaps due to dilated endoplasmic reticulum or golgi vesicles, was seen throughout the cytoplasm in more than 90% of tempo-treated cells, making it very difficult to identify membranous organelles. Recent evidence indicates that membrane blebbing and caspase activation are not in the same linear cascade of apoptosis (Huot, J. et al., 1998, *J. Cell Biol.* 143, 1361–1373. Consistent with this information, bleb formation was not noticed in tempo-treated cells. Together, these findings support the view of tempo-induced apoptosis in LNCaP cells.

EXAMPLE 11

A significant decline in tumor growth rate was noted in tempo-treated group as compared to control vehicle group (10% ethanol). These in vivo data suggest the possibility of an anti-tumor activity of tempo (FIGS. 13A, 13B1, 13B2).

DISCUSSION

This study reports, for the first time to our knowledge, signal transduction mechanisms of cellular response to two nitroxides, tempol and tempo, well known for their antioxidant properties. Initially, we hypothesized that since ERK pathway is used by a wide variety of cell types for transducing survival or proliferative signals, the antioxidant effects of tempol and tempo may be complemented by stimulation of the ERK-signaling pathway. Previous in vitro studies suggested that at least 5–10 mM tempol is required to provide radioprotection, and protection factor as high as 2.2 was achieved with 100 mM tempol (15). Our data showing activation of ERK1 by tempol (10 mM) is consistent with these and other reports of a protective role of tempol against radiation-induced mutagenicity and double strand breaks, and hydrogen peroxide induced mutagenicity (Hahn, S. M., 1992, supra; Hahn, S. M. et al., 1994, *Cancer Res.* 54, (suppl.) 2006s–2010s; DeGraff, W. G. et al., 1992, *Environ. Mol. Mutagen.* 19, 21–26; DeGraff, W. G. et al., et al., *Free Radical Biol. Med.* 13, 479–487). Surprisingly, however, tempo (10 mM) had no detectable effect on ERK1 activity, suggesting that a dissociation may also exist between ERK-signaling and antioxidant activity of certain nitroxides.

Enhanced protein tyrosine phosphorylation, generation of ceramide, activation of SAPK and induction of apoptosis by tempo are unexpected and novel observations. One possibility for further evaluation is that there may be differential intracellular reduction rate of tempol vs. tempo. In this situation, tempo-treated cells may have higher tempo free radical concentration. Free radicals, as second messengers, would the find appropriate cellular targets and turn on a signaling pathway. In this context, it is noteworthy that addition of platelet-derived growth factor (PDGF) to vascular smooth muscle cells results in increased intracellular levels of hydrogen peroxide and reactive oxygen species (ROS), and these events have been correlated with PDGF-induced tyrosine phosphorylation, MAPK stimulation, and DNA synthesis (Sundaresan, M. et al., 1995, *Science* 270, 26–299). In other reports, induction of protein tyrosine phosphorylation in neutrophils is dependent on NADPH oxidase activation (Fialkow, L. et al., 1993, *J. Biol. Chem.* 268, 17131–17137), and stimulation of as-yet unidentified protein tyrosine kinases has been linked to apoptotic death of B-lymphocytes (Uckun, F. M. et al., 1992, *Proc. Natl. Acad. Sci. U.S.A.* 89, 9005–9009). The short time required to observe the apoptosis (2 h) (FIGS. 7A1, 7A2, 7A3, 7B1, 7B2, 7C1, 7C2, 7C3, 7D1, 7D2, 7E1, 7E2, 7E3, 7F1, 7F2), suggests that cell cycle, DNA synthesis, or significant transcription/translation may not be a pre-requisite for tempo-initiated cell death. It seems possible that post-translational modification of existing proteins required for the induction of apoptosis is regulated by free-radical-mediated protein kinase pathway(s) involving SAPK.

Endogenous sphingolipid metabolites such as ceramides and sphingosines have been recognized as lipid mediators of cell growth, differentiation and apoptosis (Haimovitz-Friedman, A. et al., 1994, supra; Obeid, L. M. et al., 1993, *Science* 259, 1769–1771; Kolesnick, R. and Golde, D. W., 1994, *Cell* 77, 325–328; Bose, R. et al., 1995, *Cell* 82, 405–414; Jarvis, W. D. et al., 1994, *Proc. Natl. Acad. Sci. U.S.A.* 91, 73–77; Pushkareva, M. et al., 1995, *Immunol. Today* 16, 294–297). Apoptosis has been suggested to be dependent or independent of ceramide release (Verheij, C. et al., 1996, supra; Westwick, J. K. et al. 1995, supra; Shirakabe, K. et al. 1997, *J. Biol. Chem.* 272, 8141–8144; Watts, J. D. et al., 1997, *Proc. Natl. Acad. Sci. U.S.A.* 94, 7292–7296), and more recently ceramide has mbeen shown to interact with mitochondria leading to generation of reactive oxygen species (Garcia-Ruis, C. et al. 1997, *J. Biol. Chem.* 272, 11269–11377). In other studies, activation of a family of cysteine proteases with specificity for aspartic acid residues, also known as caspases, has been tightly linked with apoptotic cell death, and this pathway involves the release of cytochrome C from mitochondria (Liu, x. et al., 1996, *Cell* 86, 147–157; Salvesen, G. S. and Dixit, V. M., 1997, *Cell* 91, 443–446). Whether ceramide generation in tempo-treated cells is due to activation of sphingomyelinase and/or ceramide synthase, or tempo-treated results in the activation of caspases are important issues currently under investigation in our laboratory.

What components are upstream of ERK and SAPK in the tempol- and tempo-initiated signaling, respectively? Tempol and tempo are uncharged nitroxides in the physiological pH range and readily cross the cell membrane; however, their concentrations in subcellular compartments differ. Tempo is approximately 200 times more lipophilic than tempol (Kocherginsky, N. et al., 1995, in *Nitroxide Spin Labels, Reactions in Biology and Chemistry*, pp 15–26, CRC Press, Boca Raton, Fla.), hence tempo would be expected to accumulate in the cell membrane to a greater extent than tempol. Thus, having an agent such as tempo (a stable free radical) localized in the cell membrane and capable of participating in redox reactions may initiate a signal transduction cascade distinct from tempol which is more water soluble and more evenly distributed throughout the cell. Although both tempol and tempo stimulated Raf-1, ERK1 activity was increased only in tempol-treated cells. Raf activation was temporal compared to ERK1. Raf-1 activity peaked at 30 min, wherein ERK activity began to rise at 15 min and continued to rise for at least up to 120 min. This lack of correlation between the kinetics of Raf-1 activation and ERK activation has been observed earlier (Kasid, U. et al., 1996, Nature 382, 813–816; Suy, S. et al., 1997, supra), and may be due to multiple effectors, including Raf-1, upstream of ERK. At present, the significance of Raf-1 activity in a nitroxide-induced response is unclear. MEK, a known physiological substrate of Raf-1 and activator of ERK (Dent, P. et al., 1992, *Science* 257, 1404–1407; Howe, L. R. et al., 1992, *Cell* 71, 335–342; Kyriakis, J. M. et al., 1992, Nature 358, 417–421; Avruch, J. et al., 1994 *Trends Biochem. Sci.* 19, 279–283; Crews, C. W. et al., 1992, *Science* 258, 478–480; Marshall, C. J., 1994, *Curr. Opin. Genet. Dev.* 4, 82–89), and SEKI, a potent activator of SAPK (Derijard, B. et al., 1995, supra; Sanchez, I. et al., 1994, supra; Johnson, N. L. et al., 1996, supra; Minden, A. et al., 1994, supra; Lin, A. et al., 1995, Science 268, 286–290) are other potential upstream targets. The regulation of MAPKs including ERK and JNK/SAPK involves sequential phosphorylations, often initiated at the cell surface by a receptor or non-receptor protein tyrosine kinase(s). Other reports have suggested a balance between ERK and SAPK activities as a determinant of cell survival or cell death (Xia, Z. et al., 1995, supra). Based on a significant increase in protein tyrosine phosphorylation within 15 min after tempo treatment compared to tempol, it is plausible to speculate the activation of a lipid-mediated signaling pathway which involves pro-apoptotic protein tyrosine kinase(s) in tempo-treated cells.

In conclusion, present studies provide evidence that (a) tempo induces a significant tyrosine phosphorylation of several as-yet unidentified proteins as compared to tempol, (b) tempol and tempo stimulate tyrosine phosphorylation and activity of Raf-1 protein kinase, (c) tempol stimulates MAPK (ERK) activity, whereas tempo is a potent inducer of SAPK phosphorylation and activity, (d) tempo, but not tempol, induces apoptotic cell death, and (e) tempo-induced cell death could be associated with ceramide generation in MDA-MB231 cells. Our findings imply that in the absence of an environmental oxidative stress, such as that induced by ionizing radiation, nitroxides tempol and tempo stimulate distinct signal transduction pathways, perhaps triggered by secondary radicals associated with cellular metabolism and differentially regulated by early events, such as the control of protein tyrosine phosphorylation and generation of ceramide.

The MAP kinase pathway is a widely used signal transduction mechanism that initiates proliferation. Hyperexpression of MAP kinase has been localized to malignant breast epithelium and metastatic cells of patients with breast cancer (Sivaraman, V. S. et al., 1997, *J. Clin. Invest.* 99, 1478–1483). Identification of compounds activating a cell death pathway(s) should then lead to their rational use in cancer therapy. The finding that tempo induces apoptosis in different cell types warrants further study. It is most interesting that an agent that exerts antioxidant activity can also induce cytotoxicity by apoptosis. Should there be a differential induction of apoptosis in human tumor versus normal cells, the use of tempo may have clinical utility. Studies are presently under way in our laboratory to explore this possibility.

What is claimed is:

1. A method for inducing cell death by activation of the caspase signaling cascade in a cell comprising administering to said cell a composition comprising 2,2,6,6-tetramethyl-1-piperidinyloxy in an amount effective to activate the caspase cascade.

2. The method according to claim 1 wherein said caspase is caspase-3.

3. A method for inducing cell death by activation of the SAPK signaling cascade in a cell comprising administering to said cell a composition comprising 2,2,6,6-tetramethyl-1-piperidinyloxy in an amount effective to activate the SAPK cascade.

4. A method for activating an apoptotic signaling cascade in a cell comprising administering to said cell a composition comprising 2,2,6,6-tetramethyl-1-piperidinyloxy in an amount effective to activate said apoptotic signaling cascade, wherein said activating results in apoptosis.

5. A method for inducing cell death for the treatment of warts and moles comprising administering to a cell of a wart or mole a composition comprising 2,2,6,6-tetramethyl-1-piperidinyloxy in an amount effective to induce death of said cell.

* * * * *